(12) United States Patent
Masters et al.

(10) Patent No.: US 12,636,661 B2
(45) Date of Patent: May 26, 2026

(54) BLOOD AND BONE MARROW FRACTIONATION DEVICES AND METHODS

(71) Applicant: Regenexx, LLC, Broomfield, CO (US)

(72) Inventors: Michael Masters, Broomfield, CO (US); Christopher Centeno, Broomfield, CO (US); Matthew Murphy, Broomfield, CO (US); Matthew Cooksey, Broomfield, CO (US); Dustin Berger, Broomfield, CO (US); Neven Steinmetz, Broomfield, CO (US)

(73) Assignee: REGENEXX, LLC, Broomfield, CO (US)

( * ) Notice: Subject to any disclaimer, the term of this patent is extended or adjusted under 35 U.S.C. 154(b) by 491 days.

(21) Appl. No.: 18/333,852

(22) Filed: Jun. 13, 2023

(65) Prior Publication Data

US 2024/0416363 A1     Dec. 19, 2024

(51) Int. Cl.
*B04B 5/04* (2006.01)
*A61M 1/36* (2006.01)
(Continued)

(52) U.S. Cl.
CPC ......... *B04B 5/0442* (2013.01); *A61M 1/3693* (2013.01); *B01D 21/262* (2013.01);
(Continued)

(58) Field of Classification Search
CPC .. G01N 1/286; G01N 1/38; G01N 2001/2866; B01F 23/51; B01F 23/53;
(Continued)

(56) References Cited

U.S. PATENT DOCUMENTS

| 6,010,627 A | 1/2000 | Hood, III |
| 6,398,972 B1 | 6/2002 | Blasetti et al. |
| (Continued) | | |

FOREIGN PATENT DOCUMENTS

| CN | 203724815 U | 7/2014 |
| CN | 108290086 B | 6/2021 |
| (Continued) | | |

OTHER PUBLICATIONS

International Search Report and Written Opinion dated Nov. 19, 2014, for International Patent Application No. PCT/US2014/049992.

(Continued)

*Primary Examiner* — Charles Cooley

(74) *Attorney, Agent, or Firm* — Quarles & Brady LLP

(57) ABSTRACT

Apparatus, system, and method embodiments provide a fractionation device for the fractionation or separation of blood or bone marrow aspirate (BMA) into one or more component layers and the efficient collection of layers of interest. The fractionation device includes a generally cylindrical sidewall, a top wall connected to an upper portion of the sidewall, a bottom wall connected to a lower portion of the sidewall, and an interior partition. The interior partition includes a sloped portion contacting the sidewall and a vertical portion contacting the top wall.

22 Claims, 22 Drawing Sheets

(51) Int. Cl.
    *B01D 21/26*        (2006.01)
    *B04B 7/04*         (2006.01)
    *B04B 11/06*       (2006.01)

(52) U.S. Cl.
    CPC ................ *B04B 7/04* (2013.01); *B04B 11/06*
             (2013.01); *B04B 2005/0485* (2013.01)

(58) Field of Classification Search
    CPC ........ B01F 29/87; B01F 33/253; B01F 33/35;
             B01F 2101/23; B01F 29/30; B01F 31/10;
             B01F 31/20; B01F 31/23; B01L 3/502;
             B01L 3/50825; B01L 2300/042; B01L
             2300/046; B02C 19/20; B04B 5/0442;
             B04B 7/04; B04B 11/06; B04B
             2005/0485; A61M 1/3693; A61M 1/029;
             A61M 2202/0427; A61M 2202/10; B01D
                               21/262
    USPC ................. 366/210–211, 130, 349; 422/550;
                                 206/219–222
    See application file for complete search history.

(56) References Cited

U.S. PATENT DOCUMENTS

| | | | |
|---|---|---|---|
| 6,893,412 B2 | 5/2005 | Saito et al. |
| 6,905,612 B2 | 6/2005 | Dorian et al. |
| 7,060,018 B2 | 6/2006 | Skinkle et al. |
| 7,445,125 B2 | 11/2008 | Ellsworth et al. |
| 7,452,344 B2 | 11/2008 | Jorgensen et al. |
| 7,520,402 B2 | 4/2009 | Ellsworth et al. |
| 7,745,106 B2 | 6/2010 | Beretta et al. |
| D632,801 S | 2/2011 | Kyle et al. |
| 7,976,796 B1 | 7/2011 | Smith et al. |
| 8,119,013 B2 | 2/2012 | Leach et al. |
| 8,133,389 B2 | 3/2012 | Dorian et al. |
| 8,177,072 B2 | 5/2012 | Chapman et al. |
| 8,348,066 B2 | 1/2013 | Ellsworth |
| 8,361,005 B2 | 1/2013 | Arm et al. |
| 8,460,227 B2 | 6/2013 | Bare et al. |
| 8,551,344 B2 | 10/2013 | Swift et al. |
| 8,696,905 B2 | 4/2014 | Coull et al. |
| 8,734,373 B2 | 5/2014 | Esteron et al. |
| 8,802,362 B2 | 8/2014 | Grippi et al. |
| 8,992,862 B2 | 3/2015 | Leach et al. |
| 9,011,800 B2 | 4/2015 | Leach et al. |
| 9,050,403 B2 | 6/2015 | Morimoto et al. |
| 9,095,665 B2 | 8/2015 | Pages et al. |
| 9,095,798 B2 | 8/2015 | Chapman et al. |
| 9,101,925 B2 | 8/2015 | Chapman et al. |
| 9,120,095 B2 | 9/2015 | O'Connell, Jr. |
| 9,138,664 B2 | 9/2015 | Leach et al. |
| 9,239,276 B2 | 1/2016 | Landrigan et al. |
| 9,259,730 B2 | 2/2016 | Serhan et al. |
| 9,329,165 B2 | 5/2016 | Ihm et al. |
| 9,393,269 B2 | 7/2016 | Harris et al. |
| 9,421,319 B2 | 8/2016 | Hwang |
| 9,535,052 B2 | 1/2017 | Singh et al. |
| 9,573,130 B2 | 2/2017 | Hassouneh et al. |
| 9,649,579 B2 | 5/2017 | Leach et al. |
| 9,696,242 B2 | 7/2017 | Walker et al. |
| 9,718,003 B1 | 8/2017 | Petrie, Jr. |
| 9,757,506 B2 | 9/2017 | Ra et al. |
| 9,775,942 B2 | 10/2017 | Jeon |
| 9,808,568 B2 | 11/2017 | O'Connell, Jr. |
| 10,040,064 B1 | 8/2018 | Petrie, Jr. |
| 10,214,764 B2 | 2/2019 | Walsh et al. |
| 10,272,445 B2 | 4/2019 | Ewer |
| 10,351,813 B2 | 7/2019 | Johnson et al. |
| 10,393,728 B2 | 8/2019 | Woodell-May |
| 10,518,275 B2 | 12/2019 | Sengun et al. |
| 10,537,888 B2 | 1/2020 | Pennie |
| 10,646,884 B2 | 5/2020 | Nash et al. |
| 10,857,549 B2 | 12/2020 | Ewer |

| | | | | |
|---|---|---|---|---|
| 10,870,110 B2 | 12/2020 | Olson | | |
| 10,871,427 B2 | 12/2020 | Hsu et al. | | |
| 10,987,672 B2 | 4/2021 | Pennie | | |
| 11,065,629 B2 | 7/2021 | Kessler et al. | | |
| 11,135,580 B1 | 10/2021 | Kowalewski | | |
| 2004/0167004 A1 | 8/2004 | Jorgensen et al. | | |
| 2004/0182795 A1 | 9/2004 | Dorian et al. | | |
| 2005/0109716 A1 | 5/2005 | Leach et al. | | |
| 2006/0094865 A1 | 5/2006 | Kapur | | |
| 2006/0251628 A1 | 11/2006 | Attawia | | |
| 2006/0278588 A1 | 12/2006 | Woodell-May | | |
| 2008/0199900 A1 | 8/2008 | Signore et al. | | |
| 2009/0014391 A1 | 1/2009 | Leach et al. | | |
| 2009/0221075 A1 | 9/2009 | Dorian et al. | | |
| 2009/0289014 A1 | 11/2009 | Hoeppner | | |
| 2010/0256595 A1 | 10/2010 | Leach et al. | | |
| 2010/0260721 A1 | 10/2010 | Mcgonaigie | | |
| 2011/0021334 A1* | 1/2011 | Leach | ................ | B01L 3/50215 |
| | | | | 494/37 |
| 2011/0036786 A1 | 2/2011 | Ellsworth | | |
| 2011/0284460 A1* | 11/2011 | Leach | ................... | A61M 1/029 |
| | | | | 210/513 |
| 2013/0095007 A1 | 4/2013 | Haubert et al. | | |
| 2013/0345038 A1 | 12/2013 | Hoeppner | | |
| 2014/0054246 A1 | 2/2014 | Landrigan et al. | | |
| 2014/0205514 A1 | 7/2014 | Hwang | | |
| 2014/0356254 A1 | 12/2014 | Lee et al. | | |
| 2015/0023939 A1 | 1/2015 | Woodell-May | | |
| 2015/0104824 A1* | 4/2015 | Walker | ................ | B01L 3/5021 |
| 2015/0273360 A1 | 10/2015 | King et al. | | |
| 2016/0298076 A1 | 10/2016 | Centeno et al. | | |
| 2017/0000826 A1* | 1/2017 | Tucker | ................ | B01D 21/262 |
| 2018/0305655 A1 | 10/2018 | Centeno et al. | | |
| 2018/0326413 A1 | 11/2018 | Walkowiak et al. | | |
| 2020/0023381 A1 | 1/2020 | Shin | | |
| 2020/0139041 A1 | 5/2020 | Zanin et al. | | |
| 2020/0246516 A1 | 8/2020 | Dorian et al. | | |
| 2020/0324285 A1 | 10/2020 | Levine et al. | | |
| 2021/0113760 A1 | 4/2021 | Heinrich | | |
| 2022/0133962 A1 | 5/2022 | Lee | | |
| 2024/0416363 A1* | 12/2024 | Masters | ............... | B01D 21/262 |

FOREIGN PATENT DOCUMENTS

| | | | | | |
|---|---|---|---|---|---|
| KR | 101225664 B1 | 9/2010 | | | |
| KR | 20110009651 A | 1/2011 | | | |
| KR | 101016166 B1 | 2/2011 | | | |
| KR | 101026599 B1 | 4/2011 | | | |
| KR | 101049201 B1 | 7/2011 | | | |
| KR | 20110079122 | 7/2011 | | | |
| KR | 101110576 B1 | 1/2012 | | | |
| KR | 101170146 B1 | 7/2012 | | | |
| KR | 101277993 B1 | 6/2013 | | | |
| KR | 101279652 B1 | 6/2013 | | | |
| KR | 101284876 B1 | 6/2013 | | | |
| KR | 200471027 Y1 | 1/2014 | | | |
| KR | 101406574 B1 | 6/2014 | | | |
| KR | 101433293 B1 | 8/2014 | | | |
| KR | 101666451 B1 | 10/2016 | | | |
| KR | 101990633 B1 | 6/2019 | | | |
| KR | 102146508 B1 | 8/2020 | | | |
| KR | 102223877 B1 * | 2/2021 | | ............... | B04B 7/04 |
| KR | 1020230034538 A | 3/2023 | | | |
| WO | WO2013066013 | 5/2013 | | | |
| WO | WO2015021189 | 2/2015 | | | |
| WO | 2016192502 A1 | 12/2016 | | | |
| WO | WO2021133992 | 7/2021 | | | |

OTHER PUBLICATIONS

European Search Report, dated Feb. 3, 2017, 11 pages.
U.S. Appl. No. 14/778,530, Office Action-Restriction-Requirement, dated Jun. 23, 2017, 7 pages.
U.S. Appl. No. 14/778,530, Non-Final Office Action dated Sep. 13, 2017, 16 pages.
U.S. Appl. No. 14/778,530, Notice of Allowance, dated Apr. 4, 2018, 16 pages.

(56)          References Cited

OTHER PUBLICATIONS

European Examination Report, EU Patent Application No. 14834894.9 dated Apr. 9, 2019; 4 pages.

Insausti et al., Stem Cells and Development, vol. 21, No. 2, pp. 260-272 (2012).

Notice of Allowance, U.S. Appl. No. 15/958,940, dated Sep. 30, 2019.

U.S. Appl. No. 17/569,738, Non-Final Office Action dated May 2, 2023, 20 pages.

International Search Report and Written Opinion, corresponding to PCT/US2024/029918, dated Sep. 4, 2024.

\* cited by examiner

10b

96

94

92

90

200

200

202

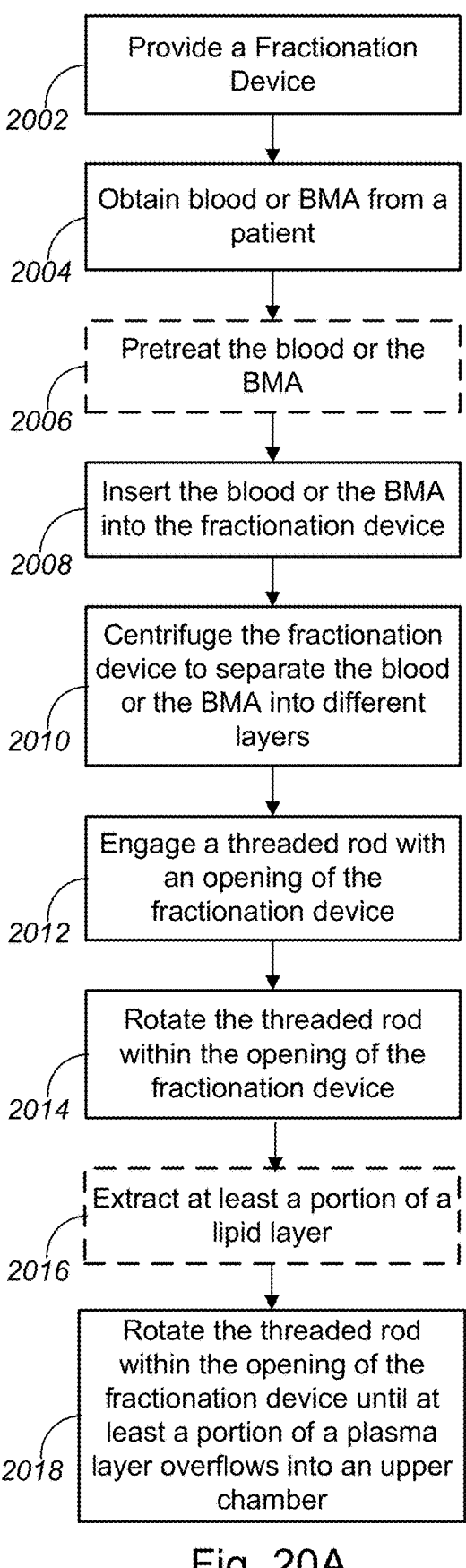

2002 — Provide a Fractionation Device

2004 — Obtain blood or BMA from a patient

2006 — Pretreat the blood or the BMA

2008 — Insert the blood or the BMA into the fractionation device

2010 — Centrifuge the fractionation device to separate the blood or the BMA into different layers 2012 — Engage a threaded rod with an opening of the fractionation device 2014 — Rotate the threaded rod within the opening of the fractionation device 2016 — Extract at least a portion of a lipid layer 2018 — Rotate the threaded rod within the opening of the fractionation device until at least a portion of a plasma layer overflows into an upper chamber

BLOOD AND BONE MARROW FRACTIONATION DEVICES AND METHODS

TECHNICAL FIELD

The embodiments disclosed herein are directed toward an apparatus, system, and method for the fractionation of blood or bone marrow aspirate. Embodiments are more particularly directed toward systems, apparatuses, and methods for a fractionation device to separate blood or bone marrow aspirate into one or more layers and provided for the efficient collection of specific layers.

BACKGROUND

Fractionation devices are used to separate blood or bone marrow aspirate (BMA) into one or more component layers or fractions (e.g., a red blood cell layer, a plasma layer, a lipid layer, a platelet rich pellet layer, or the like). The blood or BMA may be separated within a fractionation device using a centrifuge. As the centrifuge spins the blood or BMA is separated into its component layers and then each of these layers may be individually extracted and subsequently processed or utilized. The blood or BMA may go through one or more cycles in the centrifuge to separate into one or more component layers. There are various known fractionation devices used to separate blood or bone marrow aspirate (BMA) into one or more component layers.

However, it may be hard to efficiently separate and individually extract desired layers of blood or BMA. Additionally, it may be hard to visualize some layers within the fractionation device.

The embodiments disclosed herein are directed toward overcoming one or more of the problems discussed above.

SUMMARY OF THE EMBODIMENTS

Apparatus, system, and method embodiments are disclosed herein that provide a fractionation device for the fractionation or separation of blood or bone marrow aspirate (BMA) into one or more component layers or fractions (e.g., a red blood cell layer, a plasma layer, a lipid layer, or the like).

One embodiment disclosed herein is a fractionation apparatus or device for the fractionation or separation of blood or (BMA) into one or more component layers or fractions. The fractionation device includes a generally cylindrical sidewall, a top wall connected to an upper portion of the sidewall, a bottom wall connected to a lower portion of the sidewall, and an interior partition. The interior partition includes a sloped portion contacting the sidewall and a vertical portion contacting the top wall. The fractionation device further includes an upper chamber defined within the fractionation device by the interior partition, the top wall, and the upper portion of the sidewall, a lower chamber defined within the fractionation device by the interior partition, an upper plunger surface of a captive plunger engaged with the sidewall, and the lower portion of the sidewall, and a lower region of the upper chamber defined by the sloped portion of the interior partition adjacent to the sidewall. Additionally, the fractionation device includes a threaded opening through the bottom wall.

Method embodiments disclosed herein can include the steps of providing a fractionation device, obtaining blood or bone marrow aspirate (BMA) from a patient, pretreating the blood or the BMA from the patient, inserting the blood or the BMA into the lower chamber of the fractionation device, and centrifuging the fractionation device to separate the blood or the BMA into different layers. The method may continue by engaging a threaded rod with the threaded opening and rotating the threaded rod within the threaded opening to cause the captive plunger to rise within the lower chamber of the fractionation device until a plasma layer overflows into the upper chamber of the fractionation device via an overflow window formed in the vertical portion of the interior partition and providing a fluid pathway between an input channel and the upper chamber. In some cases, the method might also include removing at least a portion of the plasma layer from the upper chamber of the fractionation device.

DESCRIPTION OF THE DRAWINGS

FIGS. 20A and 20B are process diagrams of a method of using the fractionation devices and counterweights of FIGS. 1-19.

DETAILED DESCRIPTION

Figure 1:
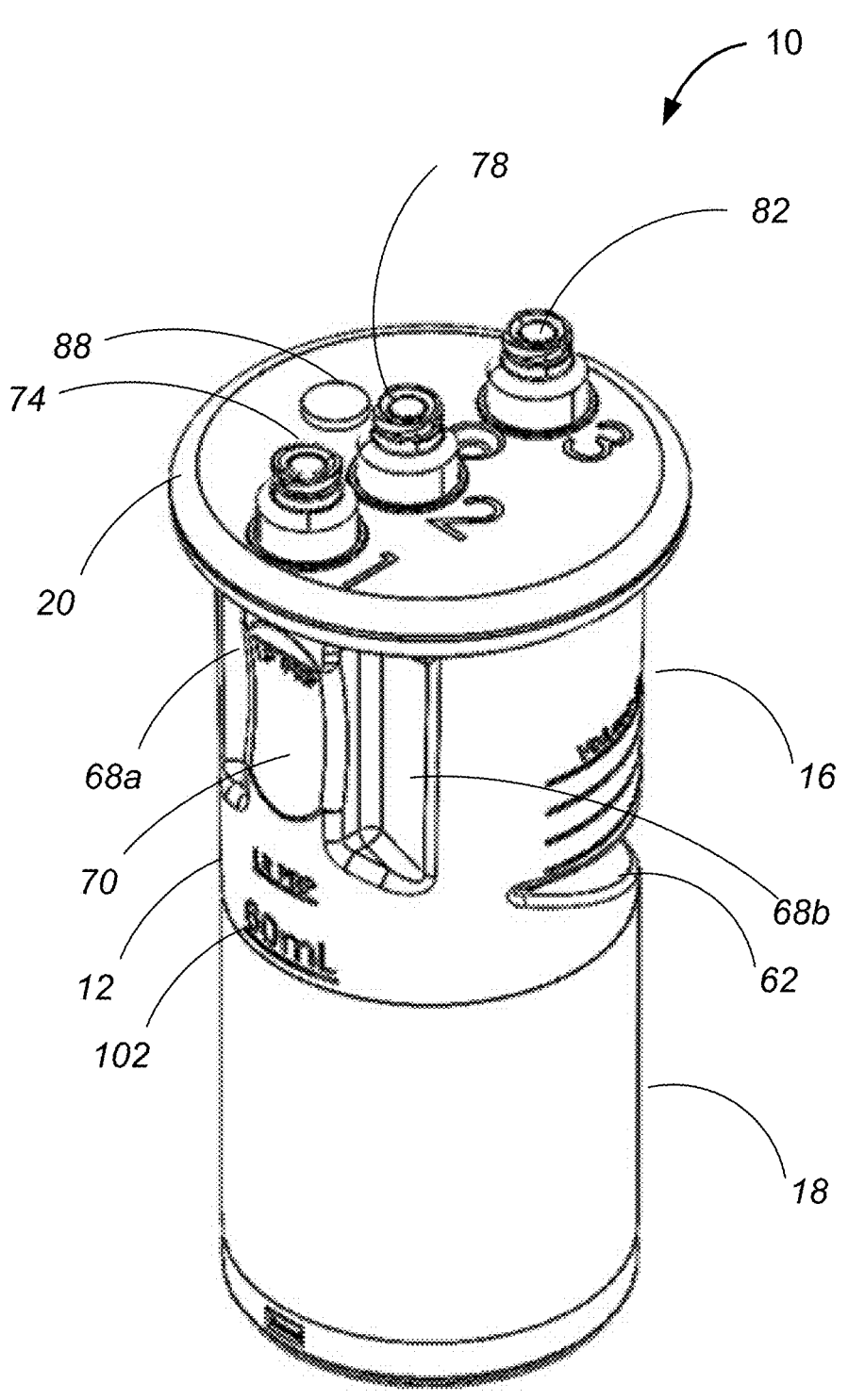
FIG. 1 is a top, front perspective view of one embodiment of a fractionation device as disclosed herein.
Figure 2:
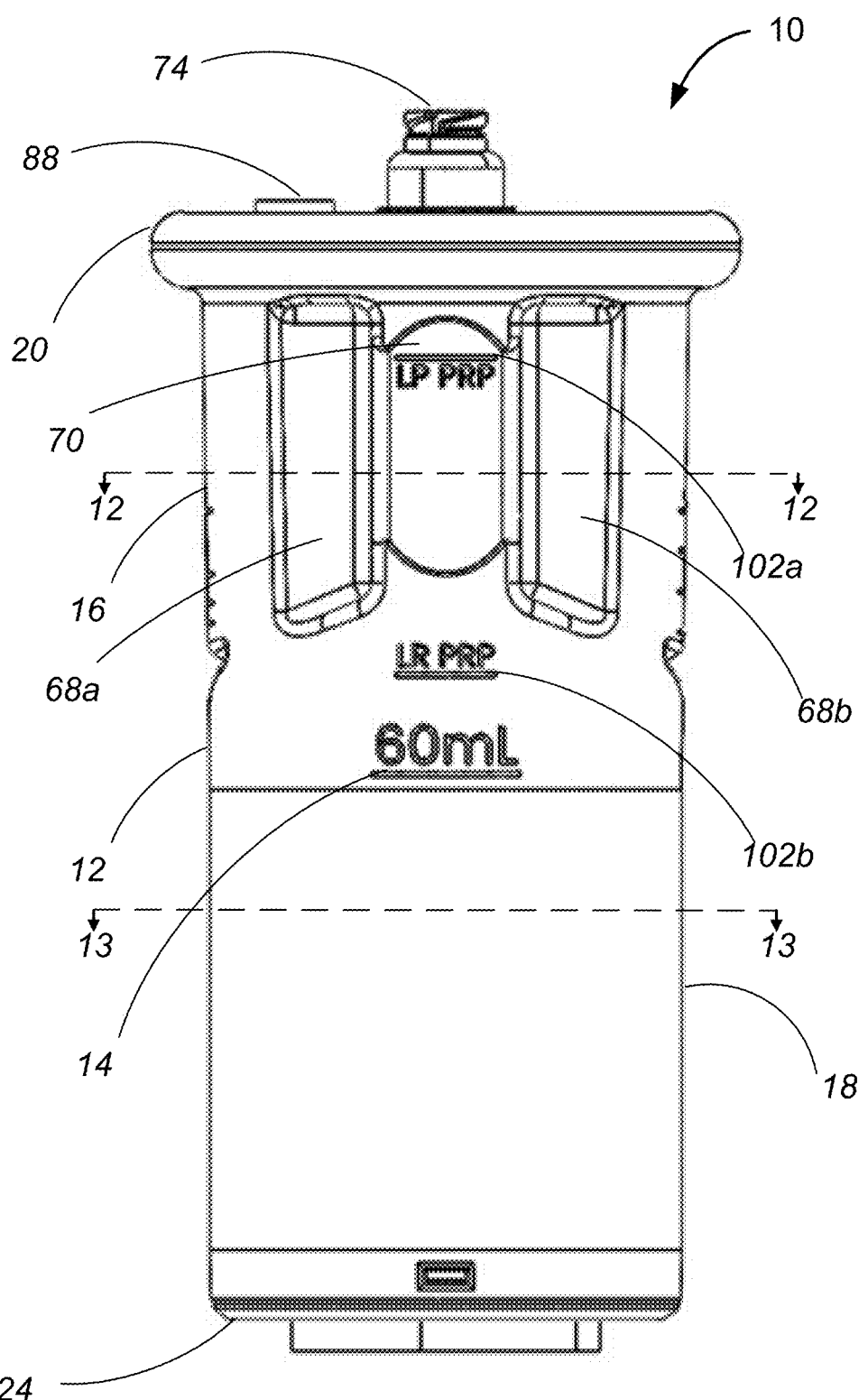
FIG. 2 is a front elevation view of the fractionation device as disclosed herein.
Figure 3:
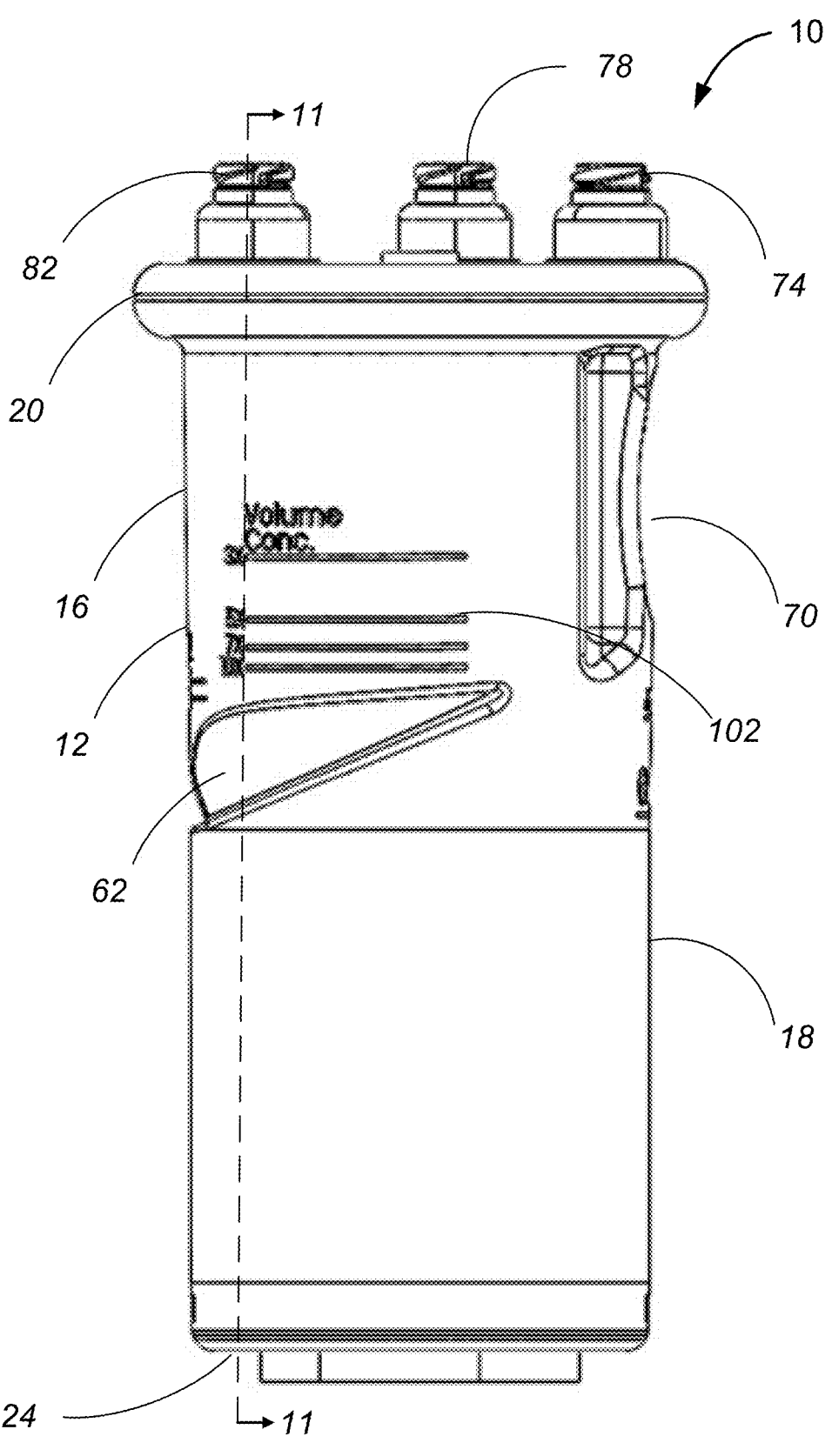
FIG. 3 is a side elevation view of the fractionation device as disclosed herein.
Figure 4:
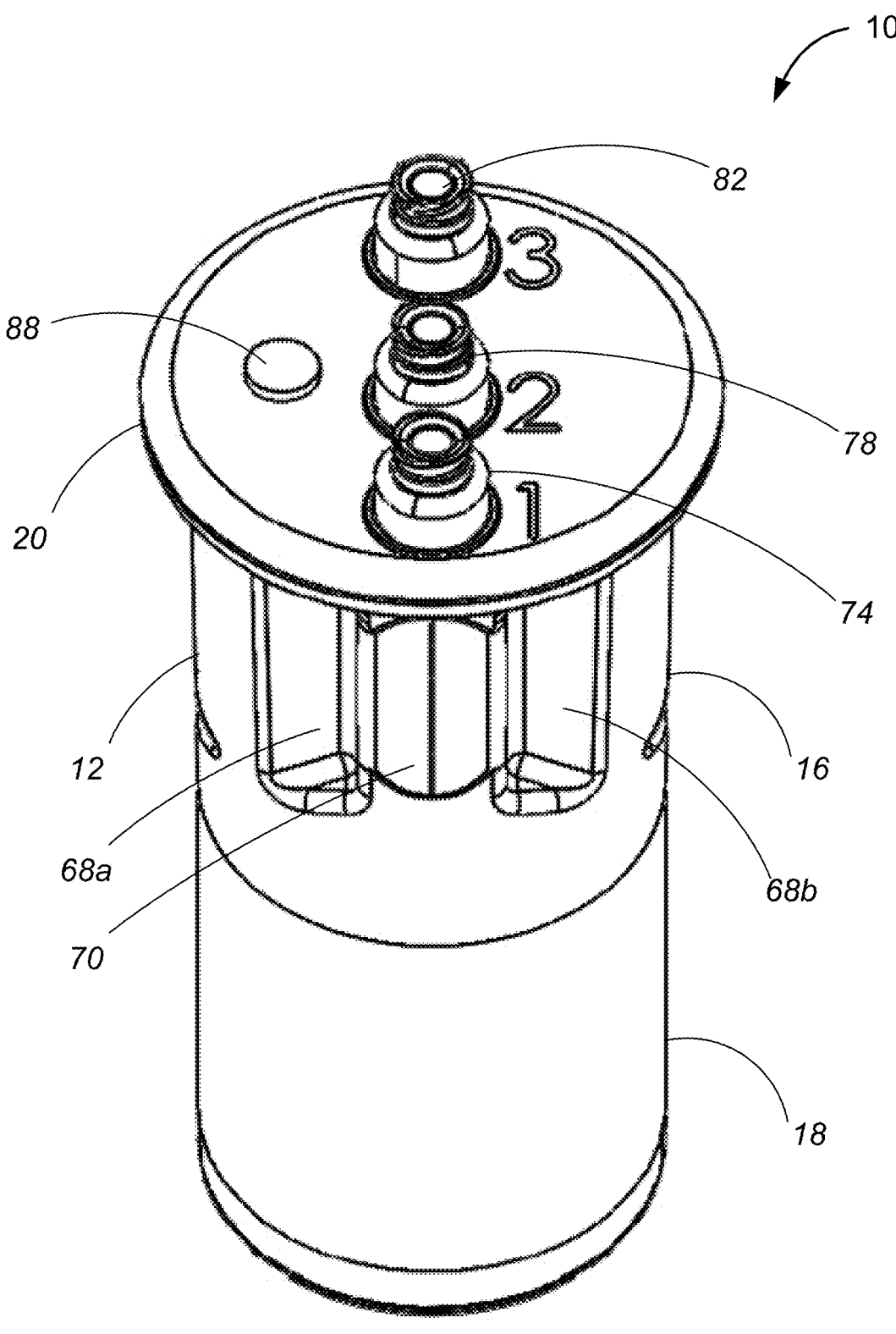
FIG. 4 is a top, front perspective view of the fractionation device as disclosed herein.
Figure 5:
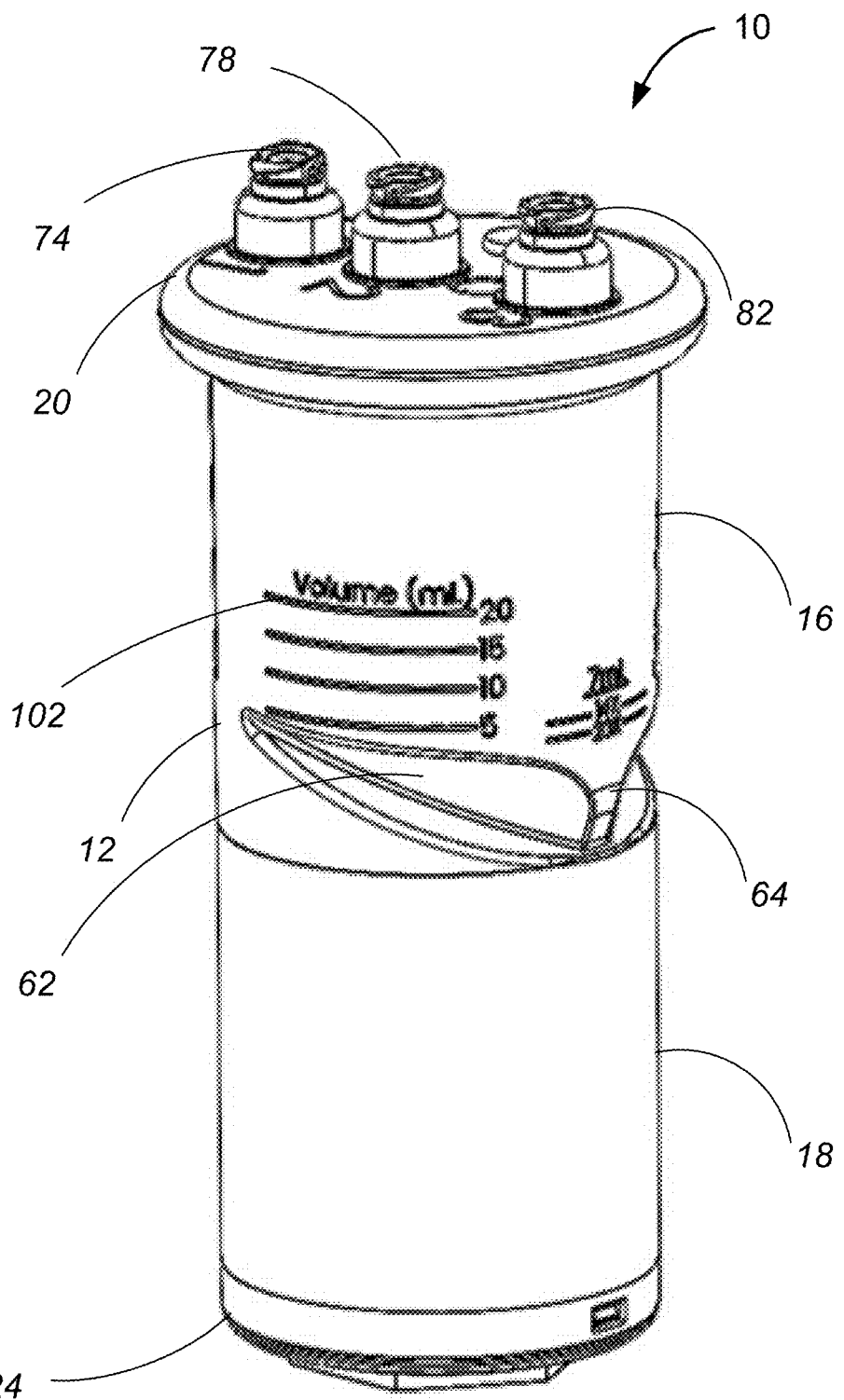
FIG. 5 is a top, back, side perspective view of the fractionation device as disclosed herein.

Unless otherwise indicated, all numbers expressing quantities of ingredients, dimensions, reaction conditions and so forth used in the specification and claims are to be understood as being modified in all instances by the term "about" or "approximately". Additionally, unless otherwise specified or limited, the terms "about" and "approximately," as used herein with respect to a reference value or ratio, refer to variations from the reference value or ratio of ±20% or less (e.g., ±15, ±10%, ±5%, etc.), inclusive of the endpoints of the range.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element," "structure," or "component" encompass elements, structures, and components comprising one unit and elements, structures and components that comprise more than one unit unless specifically stated otherwise. Unless specified or limited otherwise, the terms "mounted," "connected," "supported," "attached,' and "coupled" and variations thereof are used broadly and encompass both direct and indirect mountings, connections, supports, and couplings.

As used herein, unless otherwise defined or limited, directional terms are used for convenience of reference for discussion of particular figures or examples. For example, references to downward (or other) directions or top (or other) positions may be used to discuss aspects of a particular example or figure, but do not necessarily require similar orientation or geometry in all installations or configurations.

In this application and the claims, any reference to blood, bone marrow, plasma, other blood derivatives including plasma, or other bodily fluids is not limiting and, in all cases, can include reference to any of blood, bone marrow, other blood derivatives including plasma, or other bodily fluids.

Fractionation devices may be used to separate blood, bone marrow aspirate (BMA), or other bodily fluids into one or more component layers or fractions. However, once the one or more layers have been separated, extracting the one or more layers from a fractionation device can be difficult. Additionally, visualizing the one or more layers within a fractionation device can be difficult.

Embodiments of the claims can address these or other issues. For example, the various apparatus, system, and method embodiments disclosed herein provide a fractionation device that can be used to separate blood or BMA into one or more component layers and provide for the efficient extraction of one or more layers of interest from the fractionation device. In general, disclosed devices include a lower chamber and an upper chamber. The blood or BMA can be easily separated into one or more component layers (e.g., a red blood cell layer, a plasma layer, a lipid layer, a platelet rich pellet layer, etc.) within one or both chambers, after one or multiple centrifuge steps. Layers of interest, including, but not limited to a plasma layer, leukocyte or white blood cell layer (the buffy coat), and platelet rich pellet or layer may be extracted using one or more ports connected to the upper chamber. As disclosed below, in some embodiments a lipid layer may be extracted using one or more ports attached to the lower chamber. Additionally, enhancements including but not limited to manufacturing the fractionation device from an optically transparent material, providing upper and lower chambers, providing a sloped portion between the chambers and other enhancements makes it easier and more efficient for a technician or other user of the fractionation device to visualize and extract the one or more component layers of interest from fractionated blood or BMA.

The phrase "fractionation" is defined herein as a process or method that results in the separation of blood, BMA, or other bodily fluid into one or more component layers. For blood, these layers may include an erythrocyte layer or red blood cell layer, a buffy coat layer or leukocyte layer, a platelet rich pellet or platelet rich layer, a leukocyte and platelet rich layer or a leukocyte and platelet rich pellet, a plasma layer, a plasma layer containing platelets, etc. Blood is not limited to only these layers and may have more or fewer layers after fractionation depending on the number of centrifuge cycles or the speed of the centrifuge cycles. For BMA, these layers may include an erythrocyte layer or red blood cell layer, a buffy coat layer or leukocyte layer, a platelet rich pellet or platelet rich layer, a leukocyte and platelet rich layer or a leukocyte and platelet rich pellet, a plasma layer, a plasma layer containing platelets, a fat or lipid layer, and others. BMA is not limited to only these layers and may have more or fewer layers after fractionation depending on the number of centrifuge cycles or the speed of the centrifuge cycles.

Accordingly, the embodiments herein generally include an apparatus, system, and methods which include a fractionation device used to separate blood or BMA into one or more layers or fractions. Although the fractionation device will be described with respect to blood or BMA, the fractionation device can be used with other bodily fluids as well and is not intended to be limited to only blood or BMA. In addition, the disclosed device embodiments include structure, apparatus, or systems that facilitate the efficient collection of fractions of interest.

Figure 8:
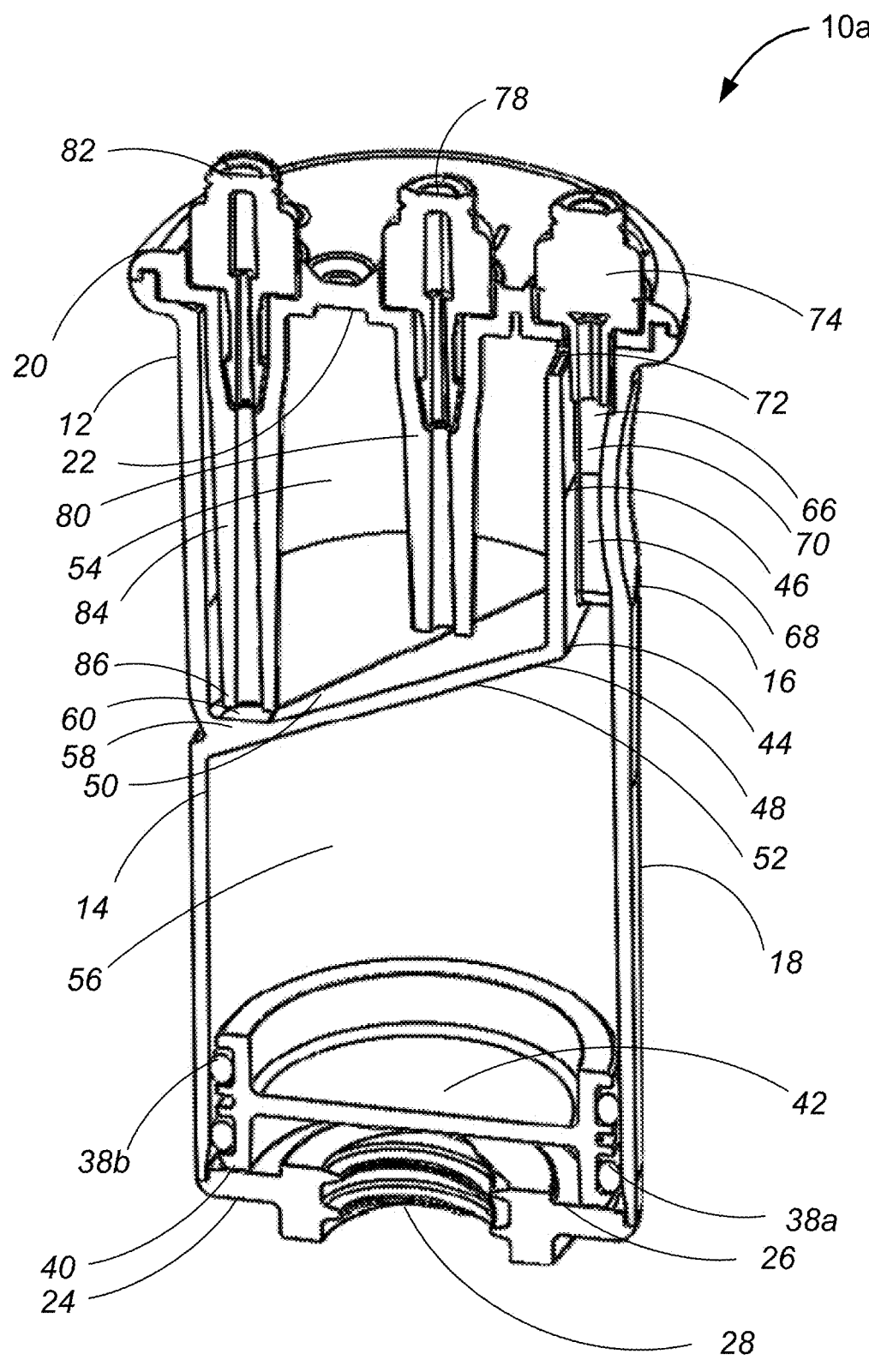
FIG. 8 is a perspective cross-sectional view of the fractionation device as disclosed herein, with the cross section taken along a front to back centerline plane.
Figure 9:
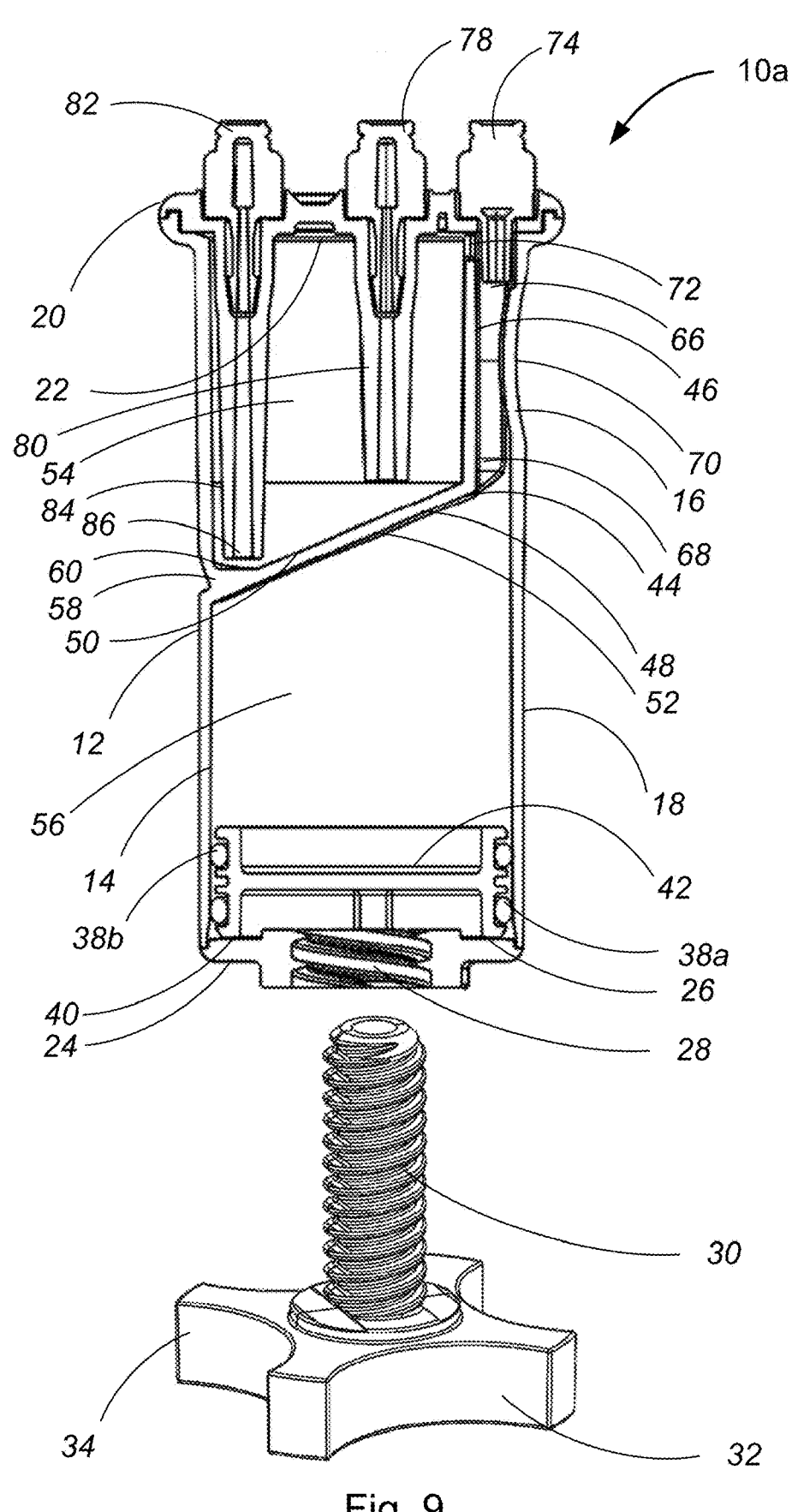
FIG. 9 is a side elevation cross sectional view of the fractionation device as disclosed herein, with the cross section taken along a front to back centerline plane.
Figure 10:
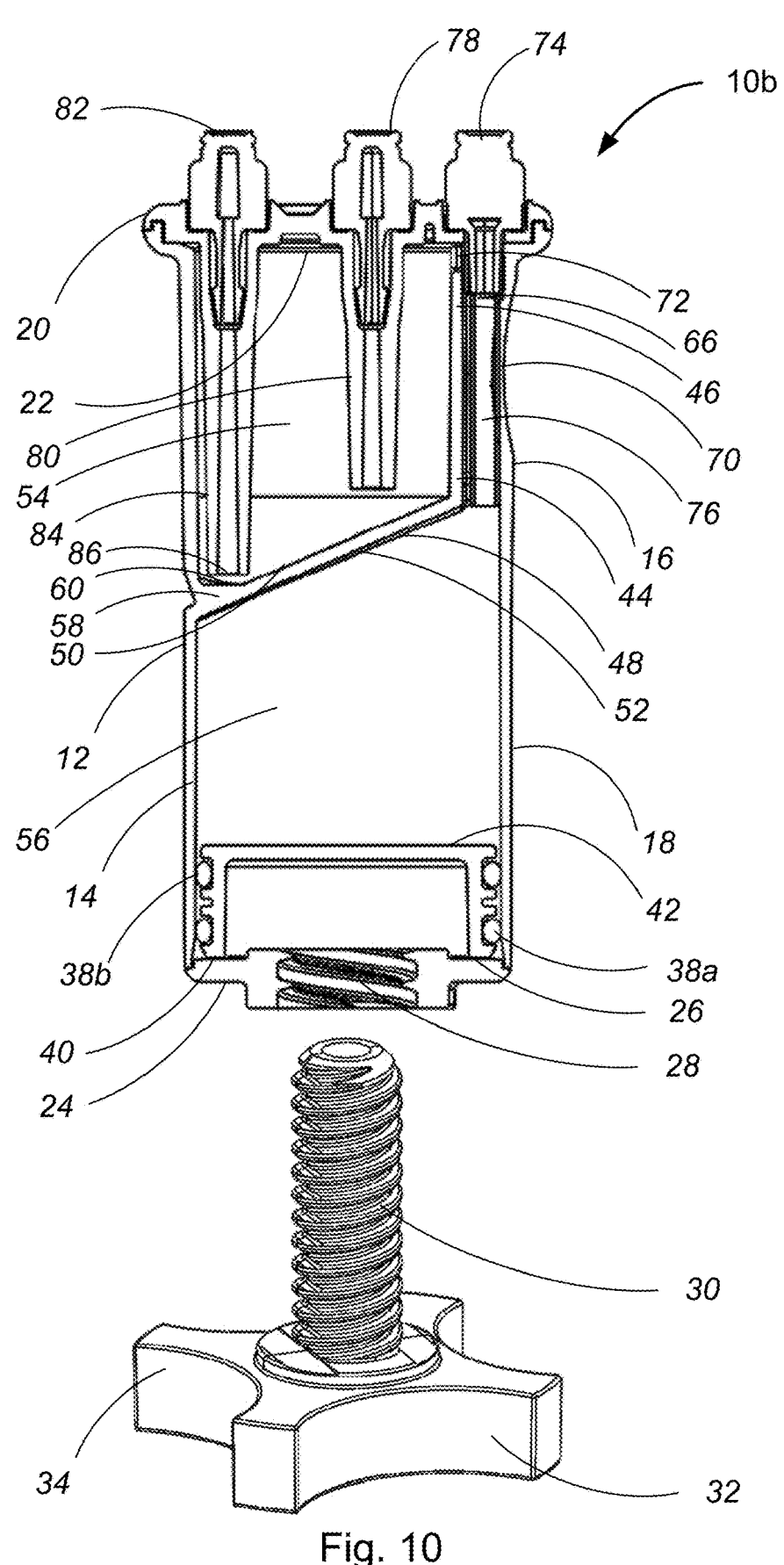
FIG. 10 is a side elevation cross sectional view of an alternative embodiment of the fractionation device as disclosed herein, with the cross section taken along a front to back centerline plane.
Figure 11:
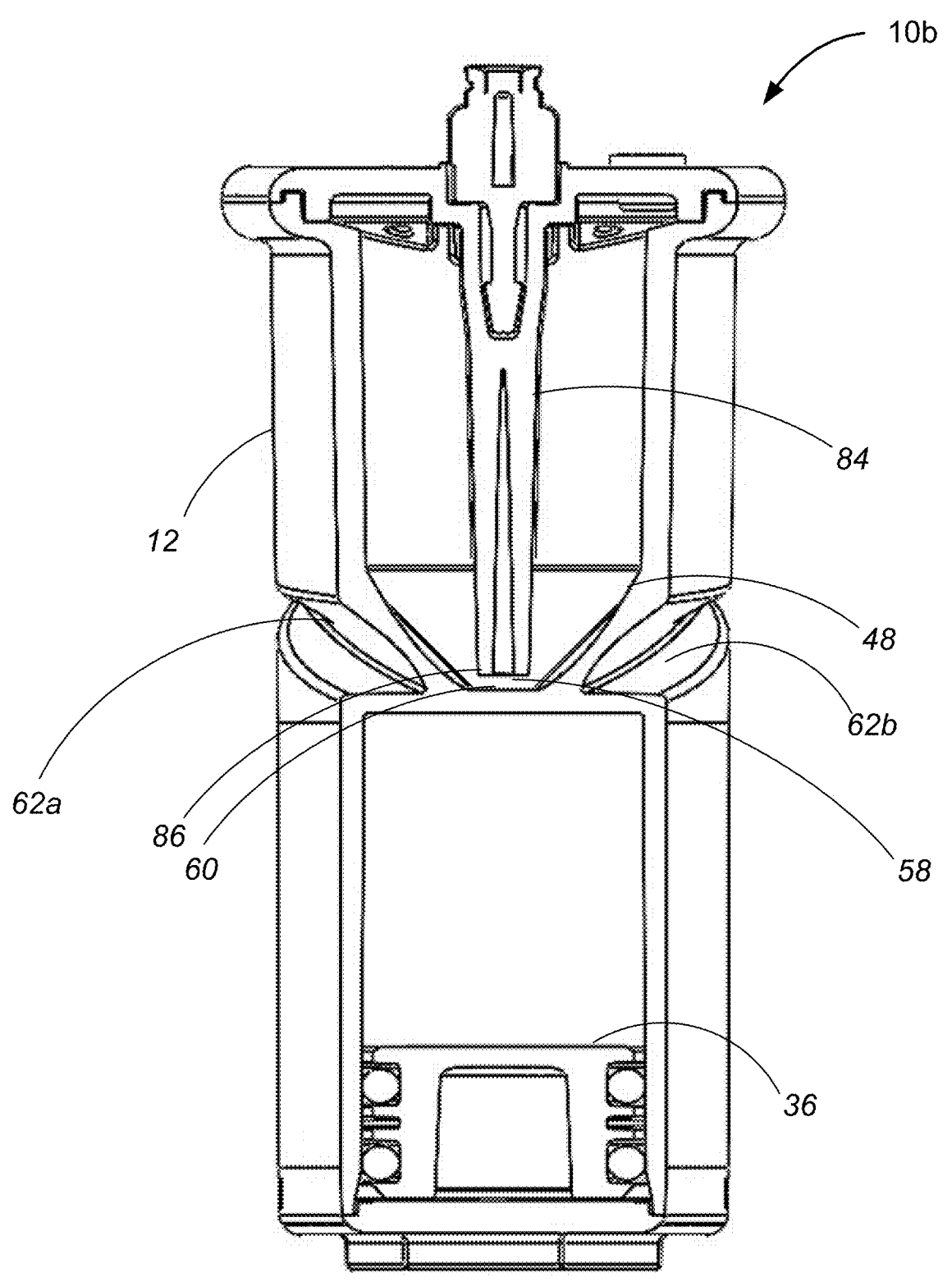
FIG. 11 is a back elevation cross sectional view of the alternative embodiment of the fractionation device as disclosed herein, with the cross section taken along a plane defined by axis 11-11 of FIG. 3.
Figure 12:
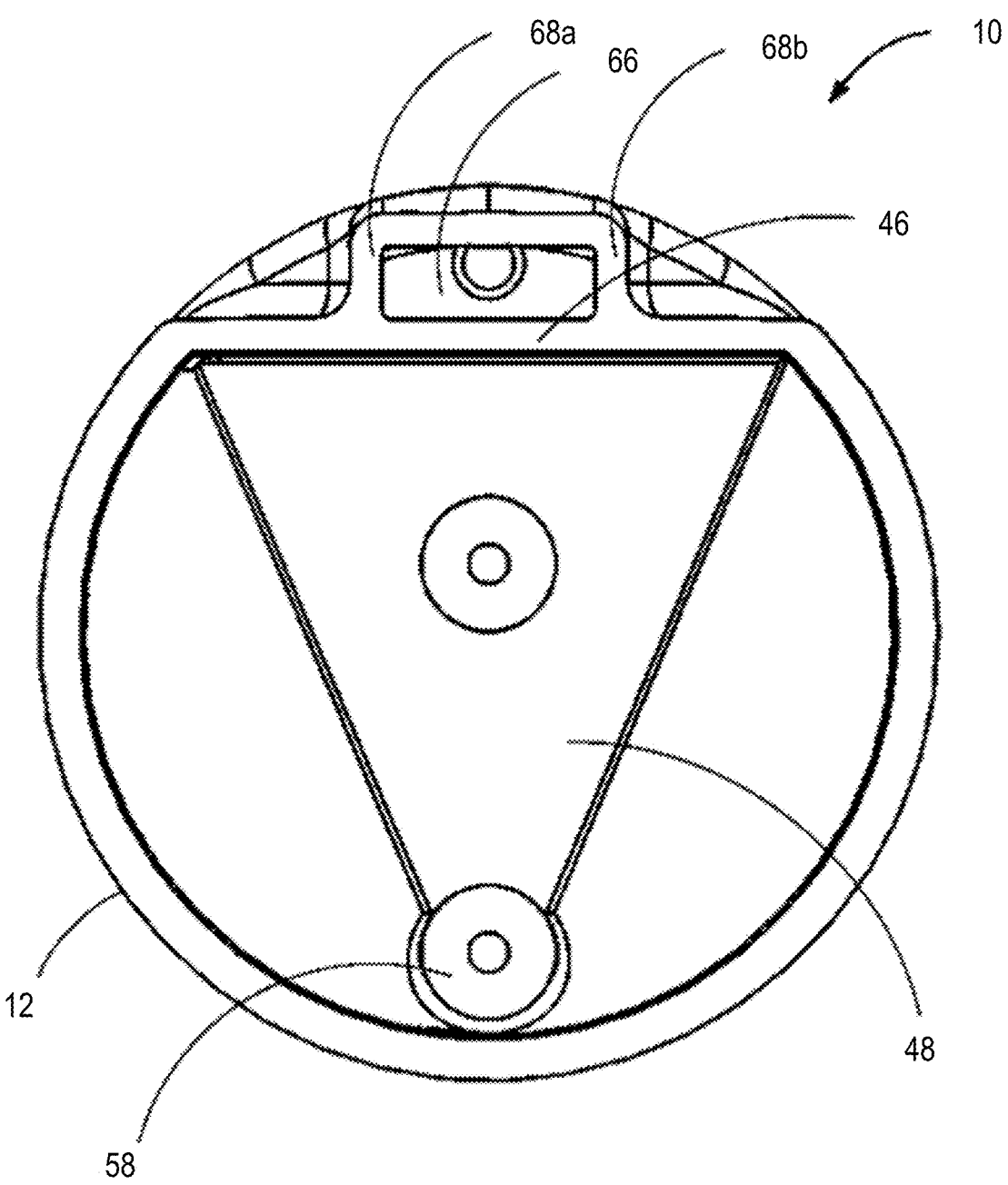
FIG. 12 is a top elevation cross sectional view of the fractionation device as disclosed herein, with the cross section taken along a plane defined by axis 12-12 of FIG. 2.
Figure 13:
FIG. 13 is a top elevation cross sectional view of the fractionation device as disclosed herein, with the cross section taken along a plane defined by axis 13-13 of FIG. 2.
Figure 13:
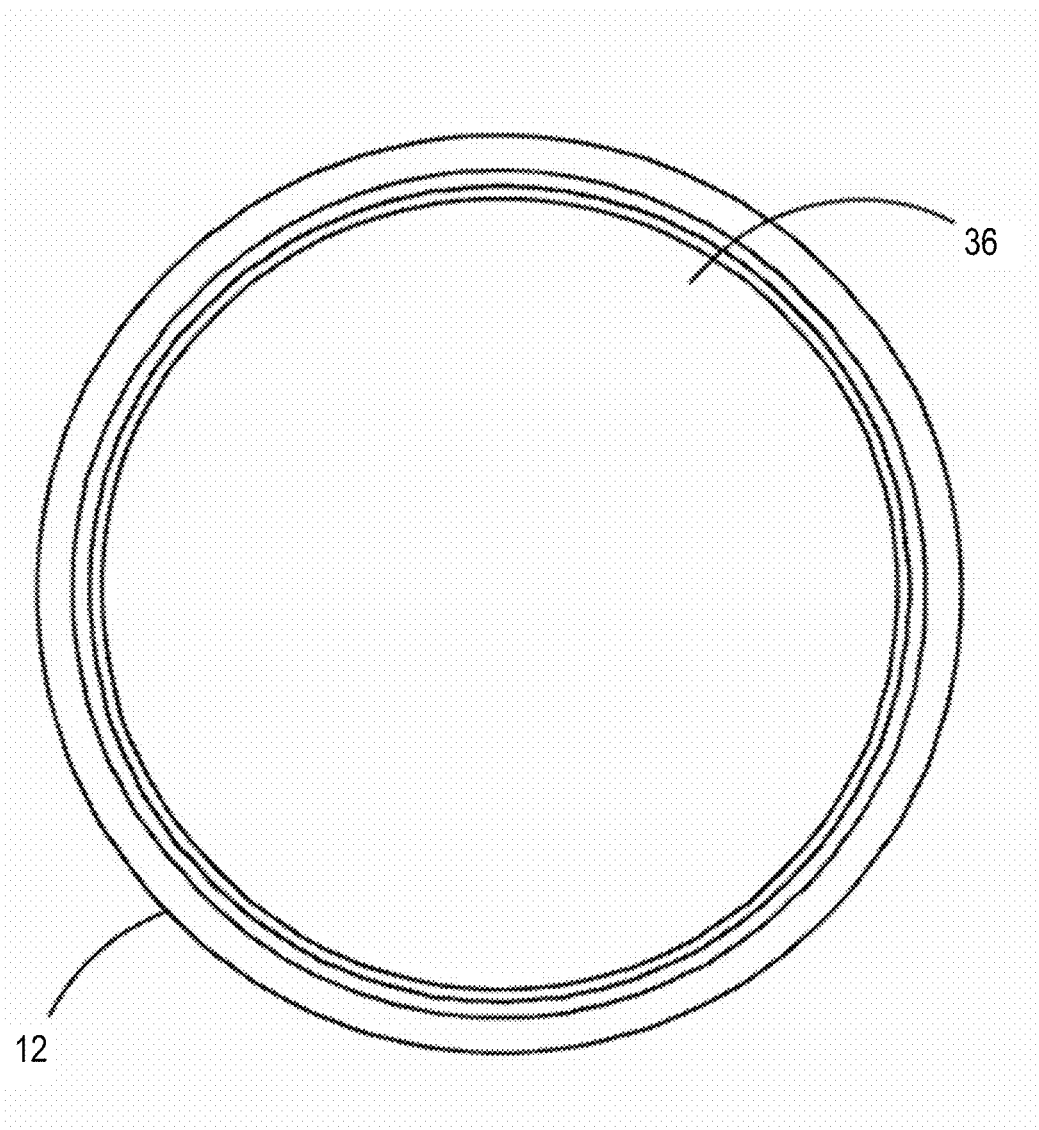
Figure 14:
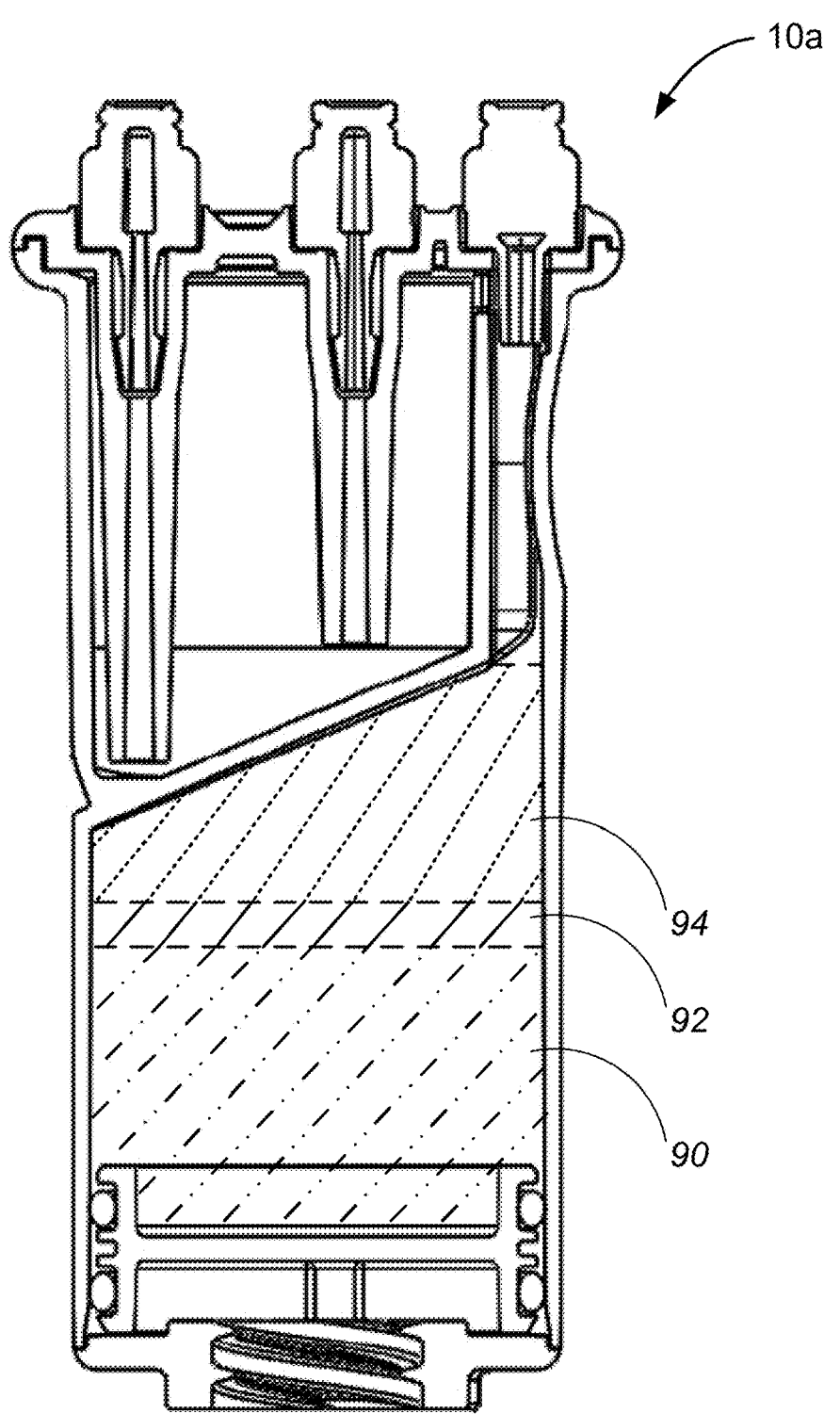
FIG. 14 is a side elevation cross sectional view of the fractionation device of FIGS. 1-9, 12, and 13 showing multiple layers of fractionated blood.
Figure 15:
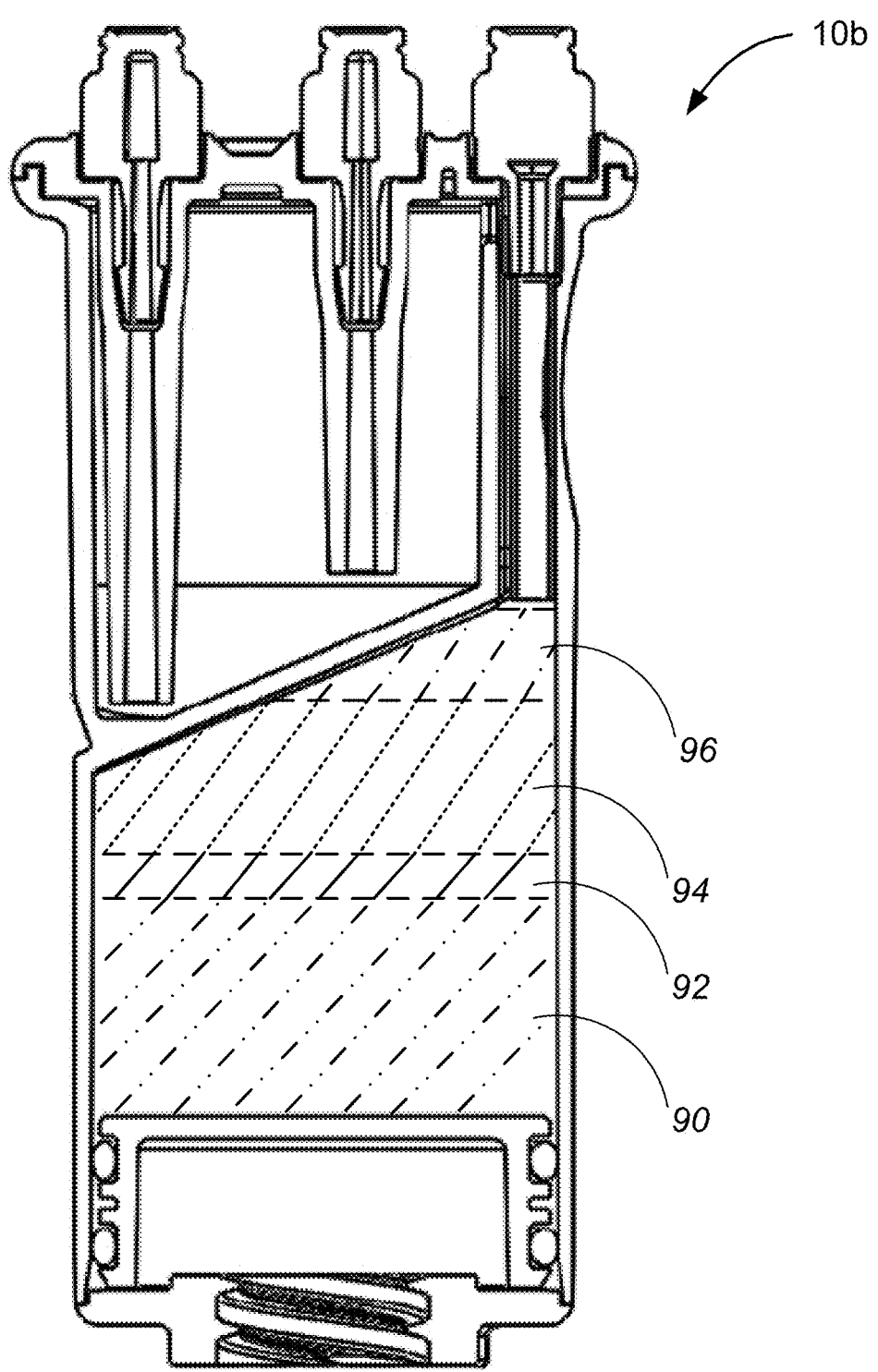
FIG. 15 is a side elevation cross sectional view of the alternative embodiment of the fractionation device of FIGS. 10 and 11 showing one or more layers of fractionated bone marrow aspirate.

FIGS. 1-16 show several views of a fractionation device 10, in accordance with various embodiments. FIGS. 8, 9, 14, and 16 show a fractionation device 10a having certain structures optimized for use with blood, while FIGS. 10, 11, and 15 show a fractionation device 10b having structures optimized for use with BMA. Many components of the fractionation device 10 overlap between the two embodiments of the fractionation device 10 for blood and for BMA. Thus, a single description and the reference number-fractionation device 10 will be used for both fractionation devices 10. Differences between the two embodiments of the fractionation device 10a and 10b will be specifically described using different reference numbers-fractionation device 10a for blood and fractionation device 10b for BMA throughout this application.

The fractionation device 10 might include a sidewall 12. The sidewall 12 might be cylindrical or tubular. However, the sidewall 12 might also be other shapes (e.g., spherical, square, octagonal, or the like). The sidewall 12 might have an inner sidewall surface 14 (shown in FIGS. 8-10) located inside the fractionation device 10. The sidewall 12 might further include an upper portion 16 of the sidewall 12 and a lower portion 18 of the sidewall 12.

In some embodiments, the sidewall 12 is formed from an optically transparent material so that that a user of the fractionation device 10 can see the through the sidewall 12 and view the material (e.g., blood, layers of the blood, BMA, or layers of the BMA, other bodily fluid, or layers of other bodily fluid) contained within the fractionation device 10. Additionally, the sidewall 12 optionally has one or more graduated lines 102 formed on the sidewall 12 (shown in FIGS. 1, 2, 3, 5, and 6). The one or more graduated lines 102 can be used to show or measure an amount of blood, BMA, or other bodily fluid located inside the fractionation device 10.

The fractionation device 10 further includes a top wall 20 connected to the upper portion 16 of the sidewall 12. The top wall 20 sealingly connects to the upper portion 16 of the sidewall 12 such that no liquid or other material can enter or escape through the top wall 20 except at prespecified locations described below. The top wall 20 might, in some embodiments, be a lid removably coupled to the upper portion 16 of the sidewall 12. Alternatively, the top wall 20 can be permanently bonded to sidewall 12. For example, the top wall 20 might be glued, bonded, welded, or integrally formed with sidewall 12. The top wall 20 includes an inner top wall surface 22 (shown in FIGS. 8-10) located inside the fractionation device 10.

The fractionation device 10 further includes a bottom wall 24 connected to the lower portion 18 of the sidewall 12. The bottom wall 24 sealingly connects to the lower portion 18 of the sidewall 12 such that no liquid or other material can enter or escape through the bottom wall 24. In some cases, the bottom wall 24 is a lid removably coupled to the lower portion 18 of the sidewall 12. Alternatively, in other cases, the bottom wall 24 is permanently bonded to sidewall 12. For example, the bottom wall 24 can be glued, bonded, welded, or integrally formed with sidewall 12. The bottom wall 24 has an inner bottom wall surface 26 (shown in FIGS. 8-10) located inside the fractionation device 10. In some cases, the inner bottom wall surface 26 does not fully enclose the lower portion 18 of the sidewall 12. In some instances, the bottom wall 24 further includes an opening 28 (shown in FIGS. 7-10). The opening 28 might be threaded and capable of receiving a threaded rod or screw 30 (shown in FIGS. 9 and 10). In other cases, the threaded rod 30 and the opening 28 might not be threaded. The threaded rod 30 can include a knob 32 attached to one end of the threaded rod 30. The threaded rod 30 has one or more prongs 34 to aid in the gripping of the knob 32 and the turning of the threaded rod 30 within the opening 28.

In some embodiments, a captive plunger 36 (shown in FIGS. 8-10) is contained within the lower portion 18 of the sidewall 12 above the inner bottom wall surface 26 of the bottom wall 24. The captive plunger 36 might be removably contained within the fractionation device 10 or permanently contained (e.g., the captive plunger 36 cannot be removed from the fractionation device 10 without modifying the captive plunger 36 or the fractionation device 10 in some way) within the fractionation device 10 once the bottom wall 24 is attached to the lower portion 18 of the sidewall 12. The captive plunger 36 can be formed from rubber, silicone, or other material capable of sealing to the inner sidewall surface 14 of the sidewall 12. In some cases, the captive plunger 36 has one or more o-rings 38, gaskets, machined surfaces, or other sealing structures capable of forming a fluid tight seal with the inner sidewall surface 14 of the sidewall 12. Preferably, in some cases the captive plunger 36 has two o-rings 38a and 38b to provide stability to the captive plunger 36 and prevent the captive plunger 36 from tipping within the sidewall 12 as the captive plunger 36 is moved within the fractionation device 10.

The captive plunger 36 includes a bottom captive plunger surface 40 and an upper captive plunger surface 42. The bottom captive plunger surface 40 of the captive plunger 36 might initially be in contact with or close to the inner bottom wall surface 26. Additionally, the threaded rod 30 is able to contact the bottom captive plunger surface 40 via the opening 28 in the bottom wall 24. When the threaded rod 30 is twisted or rotated within or pushed into opening 28 and contacts the bottom captive plunger surface 40 of the captive plunger 36, the captive plunger 36 is pushed upward within the fractionation device 10 causing blood, BMA, or other bodily fluid to rise within the fractionation device 10. In some cases, the threads of the opening 28 and the threaded rod 30 might be sized or spaced such that turning the threaded rod 30 a specific amount causes the captive plunger 36 to rise a specific amount. Additionally or alternatively, the one or more prongs 34 of the knob 32 might be spaced or oriented such that turning the knob 32 a specific amount relative to the prongs 34 (e.g., quarter turn, half turn, full turn, etc.) causes the captive plunger 36 to rise a specific amount.

The fractionation device 10 additionally includes an interior partition 44 (shown in FIGS. 8-12) located inside the fractionation device 10. The interior partition 44 has a vertical portion 46 contacting the inner top wall surface 22 of the top wall 20 and a sloped portion 48 contacting the inner sidewall surface 14. In some cases, the vertical portion 46 extends parallel to the sidewall 12. The sloped portion 48 might be sloped about 1 to 89 degrees, or more typically 20 to 70 degrees, or preferably, 20 to 30 degrees relative to a horizontal plane extending through the top wall 20 or the bottom wall 24. The interior partition 44 includes an upper interior partition surface 50 and a lower interior partition surface 52.

The fractionation device 10 includes an upper chamber 54 and a lower chamber 56 (shown in FIGS. 8-11). The upper chamber 54 is defined within the fractionation device 10 by the upper interior partition surface 50 of the interior partition 44, the inner top wall surface 22 of the top wall 20, and the inner sidewall surface 14 of the upper portion 16 of the sidewall 12. The lower chamber 56 is defined within the fractionation device 10 by the lower interior partition surface 52 of the interior partition 44, the upper captive plunger surface 42 of the captive plunger 36, and the inner sidewall surface 14 of the lower portion 18 of the sidewall 12.

The fractionation device 10 additionally includes a lower region 58 of the upper chamber 54. The lower region 58 of the upper chamber 54 is defined by the location where the upper interior partition surface 50 of the sloped portion 48 is adjacent to or contacts the inner sidewall surface 14 of the sidewall 12. In some instances, the lower region 58 comprises a flat portion 60 which is flat relative to or parallel to a horizontal plane extending through the top wall 20 or the bottom wall 24. Alternatively, in other cases, the upper interior partition surface 50 of this lower region 58 is sloped about 1 to 89 degrees, or more typically 20 to 70 degrees, or preferably, 20 to 30 degrees relative to a horizontal plane extending through the top wall 20 or the bottom wall 24.

In some embodiments, the fractionation device 10 includes one or more sloped indentations 62 in the sidewall 12. In some cases, the fractionation device 10 includes two sloped indentations 62a and 62b (shown in FIGS. 6, 7, and 11). The sloped indentations 62 define the sloped portion 48 of the interior partition 44. In a non-limiting example, as the sloped portion 48 nears the lower region 58, the sloped indentations 62a and 62b restrict a horizontal cross-section of sloped portion 48 causing the sloped portion 48 to become narrower toward the lower region 58 (shown in FIGS. 11 and 12). In other words, the sloped portion 48 is wider toward the vertical portion 46 of the interior partition 44 and narrower toward the lower region 58 of the interior partition 44. By narrowing the sloped portion 48 as it approaches the lower region 58, it becomes easier to visualize a platelet rich pellet layer and/or leukocyte and platelet rich pellet layer 100 of the blood or BMA (shown in FIG. 16) that is collected in the lower region 58. Additionally, narrowing the sloped portion 48 as it approaches the lower region 58 makes it easier to collect the platelet rich pellet layer and/or leukocyte and platelet rich pellet layer 100 as the platelet rich pellet layer and/or leukocyte and platelet rich pellet layer 100 is concentrated at the narrow portion of the lower region 58 rather than spread over a large surface.

Figure 6:
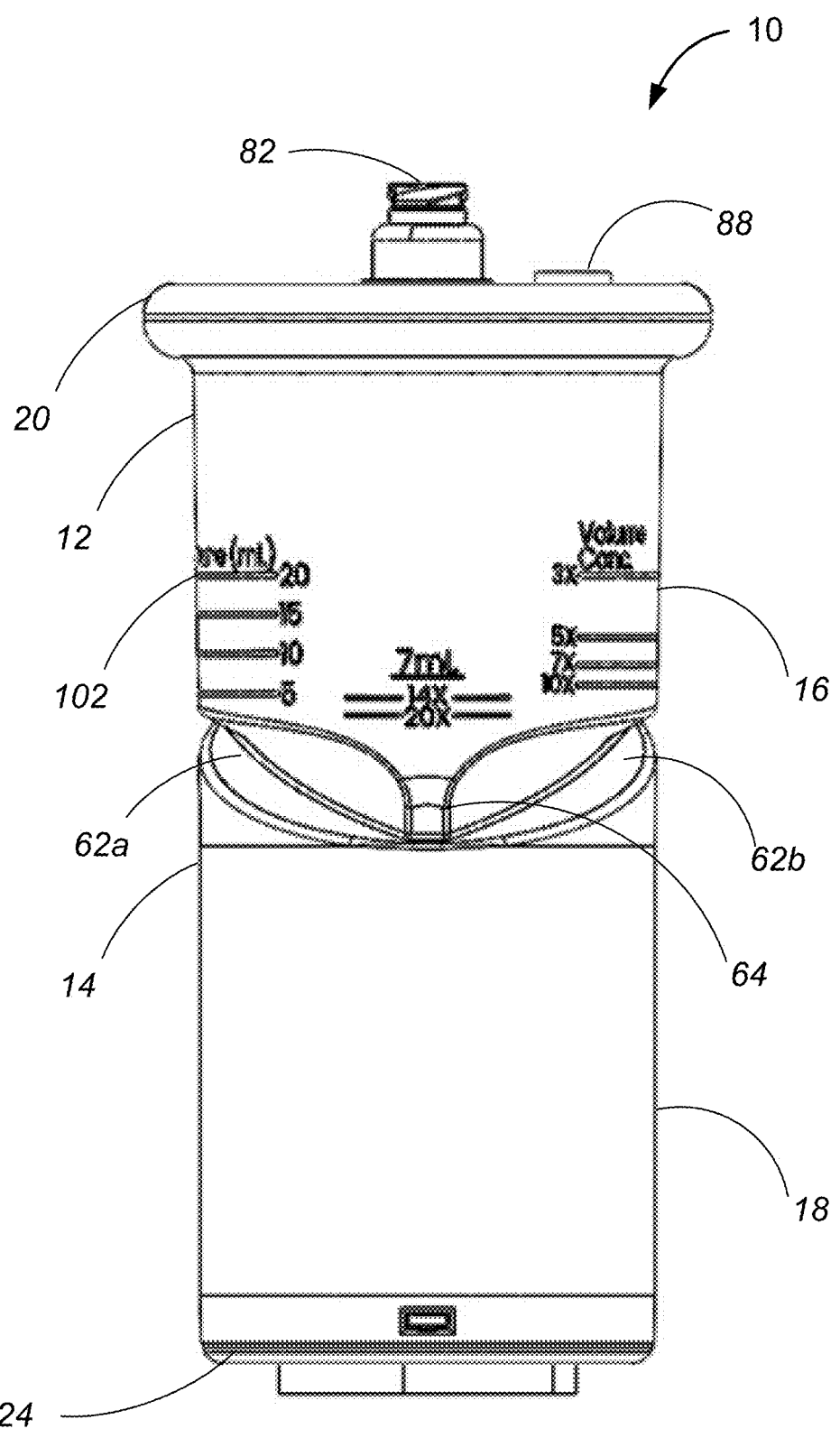
FIG. 6 is a rear elevation view of the fractionation device as disclosed herein.
Figure 7:
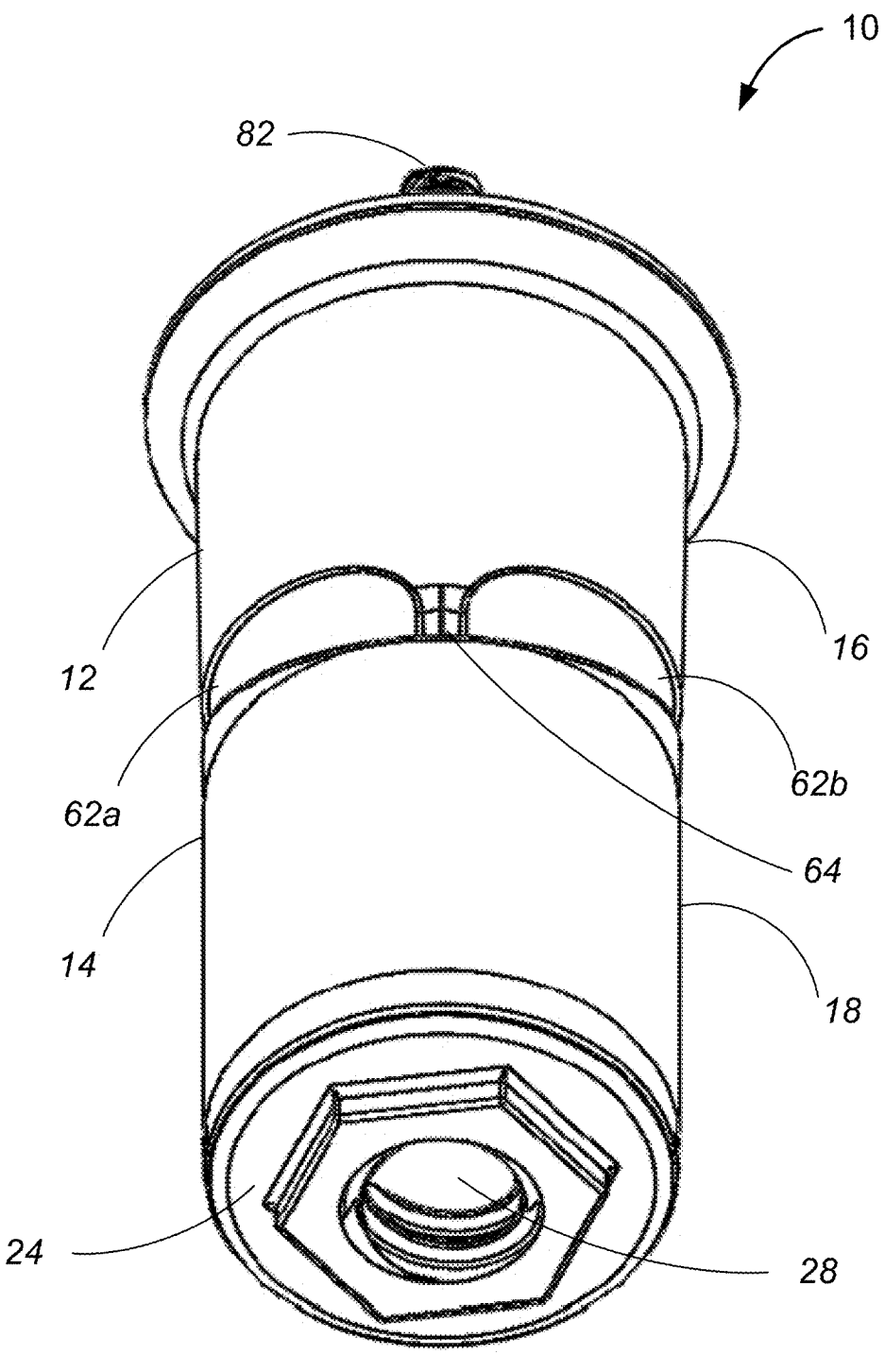
FIG. 7 is a bottom, back perspective view of the fractionation device as disclosed herein.

Additionally, in order to aid in the visualization of a platelet rich pellet layer and/or leukocyte and platelet rich pellet layer 100 of the blood or BMA that is collected in the lower region 58, the fractionation device 10 might further include a viewing window 64 (shown in FIGS. 6 and 7). The viewing window 64 optionally includes a magnifier to enhance the visibility of the platelet rich pellet layer and/or leukocyte and platelet rich pellet layer 100 of the blood or BMA.

The fractionation device 10 includes an input channel 66 extending from the top wall 20 into the lower chamber 56. The input channel 66 is defined in part by the vertical portion 46 of the interior partition 44 and the inner sidewall surface 14 of the sidewall 12. The input channel 66 might further be defined by one or more channel indentations 68 restricting a horizontal cross section on the input channel 66 (shown in FIGS. 1, 2, and 4). The one or more channel indentations 68 extend from the inner sidewall surface 14 and contact the vertical portion 46 on the interior partition 44. In some cases, the one or more channel indentations 68 include a first channel indentation 68a and a second channel indentation 68b such that the input channel 66 is defined and restricted on four sides by the inner sidewall surface 14 of the sidewall 12, the vertical portion 46 of the interior partition 44, the first channel indentation 68a, and the second channel indentation 68b.

In various instances, the sidewall 12 might optionally have a sidewall indentation 70 (shown in FIGS. 8-10) causing a portion of the sidewall 12 or a portion of the inner sidewall surface 14 to extend toward the vertical portion 46 of the interior partition 44 within the input channel 66. By adding the sidewall indentation 70, blood, BMA, or other bodily fluids may easily flow down the input channel 66 along the sidewall indentation 70 reducing hemolysis of the blood, BMA, or other bodily fluids and the number of bubbles formed within the blood, BMA, or other bodily fluids.

The fractionation device 10 includes an overflow window 72 (shown in FIGS. 8-10) formed in the vertical portion 46 of the interior partition 44 and providing a fluid pathway between the input channel 66 and the upper chamber 54. When the threaded rod 30 is twisted within the opening 28 in the bottom wall 24 contacting the bottom captive plunger surface 40 of the captive plunger 36, the captive plunger 36 rises within the fractionation device 10 causing the blood, BMA, or other bodily fluid to rise through the input channel 66 and eventually spill over from the lower chamber 56 into the upper chamber 54 via the overflow window 72. In other words, as the user twists the threaded rod 30, the user pushes the layers (e.g., layers 92 and 94 of FIGS. 14 and 15) through the input channel 66 defined and restricted on four sides by the inner sidewall surface 14 of the sidewall 12, the vertical portion 46 of the interior partition 44, the first channel indentation 68a, and the second channel indentation 68b. Defining and restricting the input channel 66 on four sides constricts the input channel 66 and creates a small cross-sectional area so that the user can more precisely and accurately control and visualize an amount of each layer (e.g., layers 92 and/or 94) or a type of layer (e.g., layers 92 and/or 94) that spills over to the upper chamber 54 through the overflow window 72.

In some instances, the input channel 66 and/or sidewall 12 has one or more graduated lines 102 formed on the sidewall 12. The one or more graduated lines 102 can be used to help a user determine how much to raise captive plunger 36 and/or layer (e.g., layers 92 and/or 94) to have a predetermined amount of each layer (e.g., layers 92 and/or 94) spill over to the upper chamber 54 through the overflow window 72. Additionally, constricting the input channel 66 on four sides allows a user to more easily visualize an amount of each layer (e.g., layers 92 and/or 94) or a type of layer (e.g., layers 92 and/or 94) that spills over to the upper chamber 54 through the overflow window 72. In a non-limiting example, a first graduated line 102a (shown in FIG. 2) may be used by a user to add a plasma layer 94 (containing platelets) to form a platelet rich pellet layer 100 in the upper chamber 54 and a second graduated line 102b (shown in FIG. 2) may be used by the user to add the buffy coat layer or leukocyte layer 92 to form a leukocyte and platelet rich pellet layer 100 in the upper chamber 54.

In some embodiments, the fractionation device 10 has a first port 74 extending through the top wall 20 and opening into the input channel 66. The first port 74 is configured to allow blood, BMA, or other bodily fluids to enter the lower chamber 56 via the input channel 66. The first port 74 might have a silicone seal or other type of hypodermic seal to seal the opening into the input channel 66 such that no liquid or other material can enter or escape through the first port 74. A needle, syringe, or a needleless Luer lock syringe, or the like may be configured to deliver blood, BMA, or other bodily fluids into the lower chamber 56 via the first port 74 and the input channel 66.

In the case of a fractionation device 10b for BMA, a lipid layer collection tube 76 (shown in FIG. 10) might be configured to extend from the first port 74 toward the lower chamber 56. The lipid layer collection tube 76 might be configured to collect or extract at least a portion of a lipid layer 96 (shown in FIG. 12) of the BMA from the lower chamber 56. A needle, syringe, or a needleless Luer lock syringe, or the like may be configured to extract at least the portion of the lipid layer 96 from the lower chamber 56 via the first port 74 and the lipid layer collection tube 76. In some embodiments, the lipid layer collection tube 76 is inserted into the fractionation device 10 after the BMA has been inserted into the fractionation device 10. Alternatively, the lipid layer collection tube 76 is configured to insert the BMA into the fractionation device 10b via the first port 74 and input channel 66.

In some cases, in order to more easily extract the lipid layer 96 via the lipid layer collection tube 76, the upper captive plunger surface 42 is located above the two o-rings 34a and 34b of the fractionation device 10b as shown in FIG. 10. By having the upper captive plunger surface 42 located above the two o-rings 34a and 34b of the fractionation device 10b, the lipid layer 96 is moved closer to the lipid layer collection tube and removed via the lipid layer collection tube 76. Alternatively, in the fractionation device 10a for blood, the upper captive plunger surface 42 of the captive plunger 36 might be located between the two o-rings 34a and 34b of the fractionation device 10a as shown in FIGS. 8 and 9.

The fractionation device 10 additionally includes a second port 78 opening into the upper chamber 54 adjacent to the vertical portion 46 of the interior partition 44 and spaced away from the lower region 58 of the upper chamber 54. The second port 78 might have a silicone seal or other type of hypodermic seal to seal the opening into the upper chamber 54 such that no liquid or other material can enter or escape through the second port 78. A plasma layer collection tube 80 might be configured to extend from the second port 78 into the upper chamber 54. The plasma layer collection tube 80 is configured to collect or extract at least a portion of an upper chamber plasma layer 98 (shown in FIG. 13) of the blood or the BMA from the upper chamber 54. A needle, syringe, or a needleless Luer lock syringe, or the like may be configured to extract at least the portion of the upper chamber plasma layer 98 of the blood or the BMA from the upper chamber 54 via the second port 78 and the plasma layer collection tube 80.

The fractionation device 10 also includes a third port 82 opening into the upper chamber 54 adjacent to the inner sidewall surface 14 of the sidewall 12 and directly above the lower region 58 of the upper chamber 54. The third port 82 might have a silicone seal or other type of hypodermic seal to seal the opening into the upper chamber 54 such that no liquid or other material can enter or escape through the third port 82. A platelet rich pellet layer and/or a leukocyte and platelet rich pellet layer collection tube 84 might be configured to extend from the third port 82 into the upper chamber 54. The platelet rich pellet layer and/or the leukocyte and platelet rich pellet layer collection tube 84 is configured to collect or extract at least a portion of a platelet rich pellet layer and/or leukocyte and platelet rich pellet layer 100 (shown in FIG. 13) of the blood or the BMA from the upper chamber 54. In some cases, the platelet rich pellet layer and/or leukocyte and platelet rich pellet layer collection tube 84 might optionally be used to resuspend or mix the platelet rich pellet layer and/or leukocyte and platelet rich pellet layer 100 within at least a portion of upper chamber plasma layer 98. A needle, syringe, or a needleless Luer lock syringe, or the like may be configured to extract at least a portion of a platelet rich pellet layer and/or leukocyte and platelet rich pellet layer 100 from the upper chamber 54 via the third port 82 and the platelet rich pellet layer and/or the leukocyte and platelet rich pellet layer collection tube 84.

In some instances, the flat portion 60 of the lower region 58 is approximately sized to be approximately a same width, diameter, or area as a first end 86 of the platelet rich pellet layer and/or the leukocyte and platelet rich pellet layer collection tube 84 (shown in FIG. 10). By having the flat portion 60 be approximately the same size as the first end 86 of the platelet rich pellet layer and/or the leukocyte and platelet rich pellet layer collection tube 84, at least a portion of a platelet rich pellet layer and/or the leukocyte and platelet rich pellet layer 100 can be more easily extracted from the fractionation device 10.

In some instances, the fractionation device 10 includes an air exchange hydrophobic filter 88. The air exchange hydrophobic filter 88 might allow the flow of air into and out of the upper chamber 54 of the fractionation device 10 without allowing liquid to enter or leave the fractionation device 10.

Figure 16:
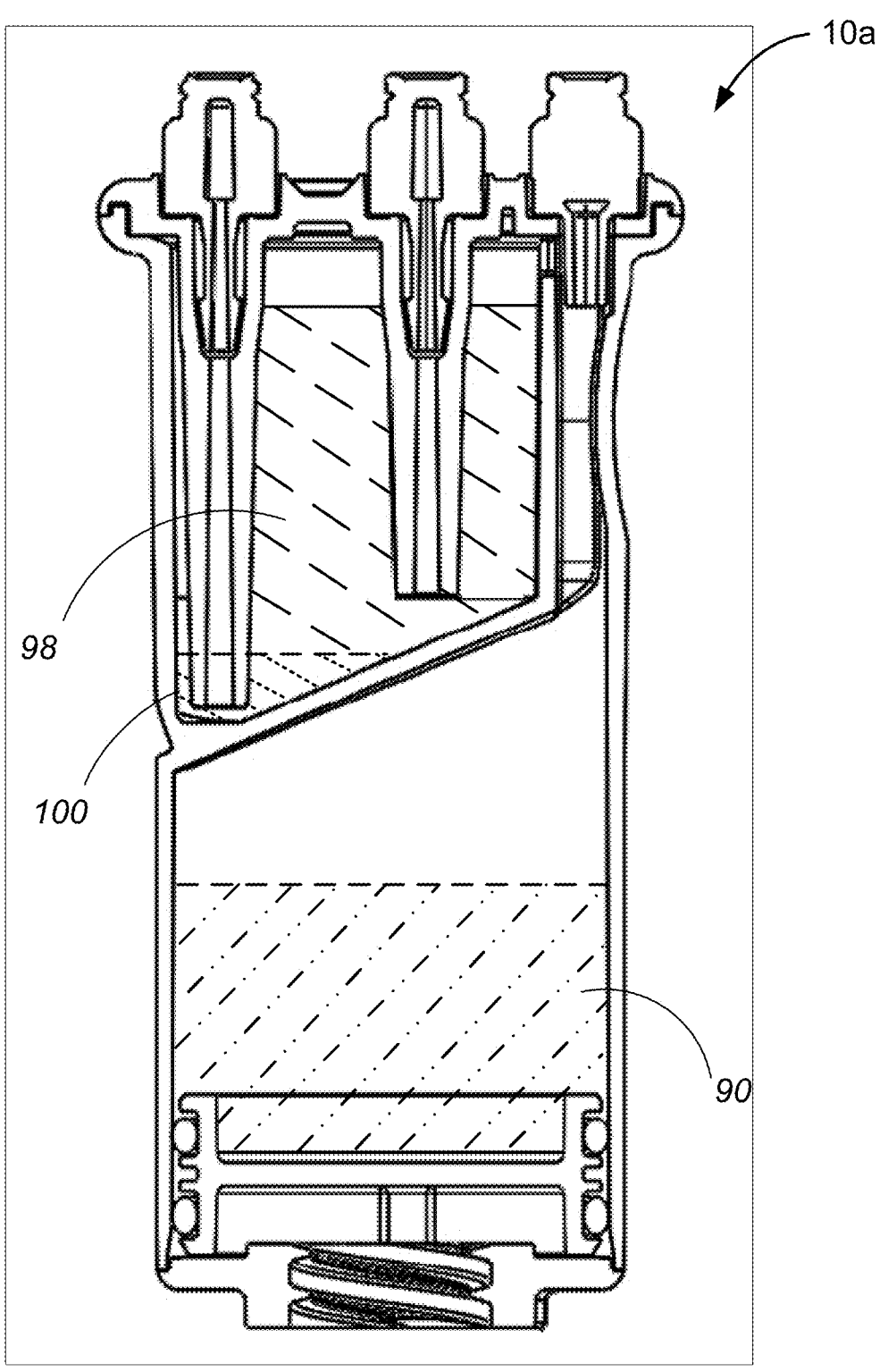
FIG. 16 is a side elevation cross sectional view of the fractionation device of FIGS. 1-9, 12, and 13 showing one or more layers of fractionated blood after a second centrifuge step.
Figure 17:
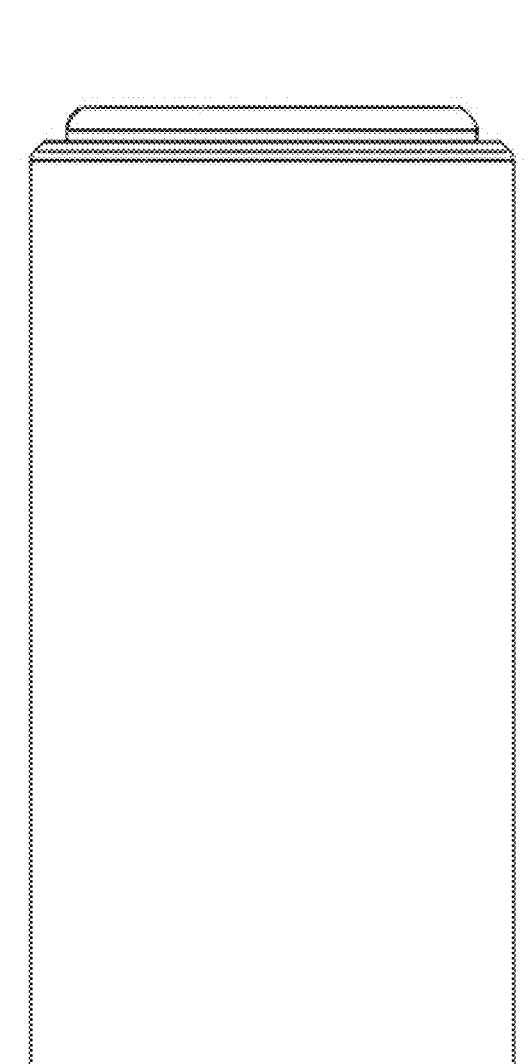
FIG. 17 is a front elevation view of a counterweight for a fractionation device as disclosed herein.
Figure 18A:
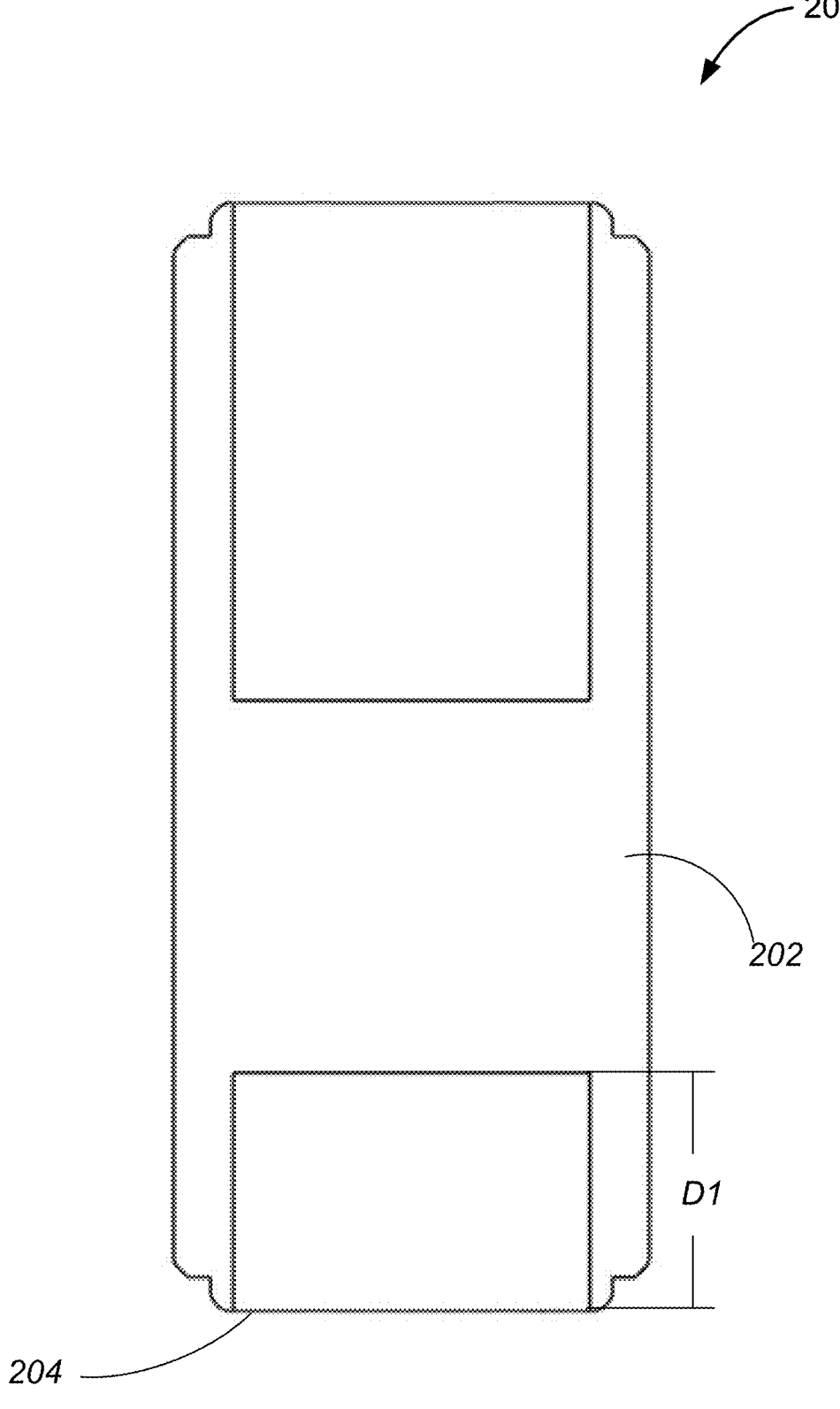
FIGS. 18A and 18B are side elevation cross sectional views of the counterweight in different orientations for a fractionation device as disclosed herein, with the cross section taken along a front to back centerline plane.
Figure 18B:
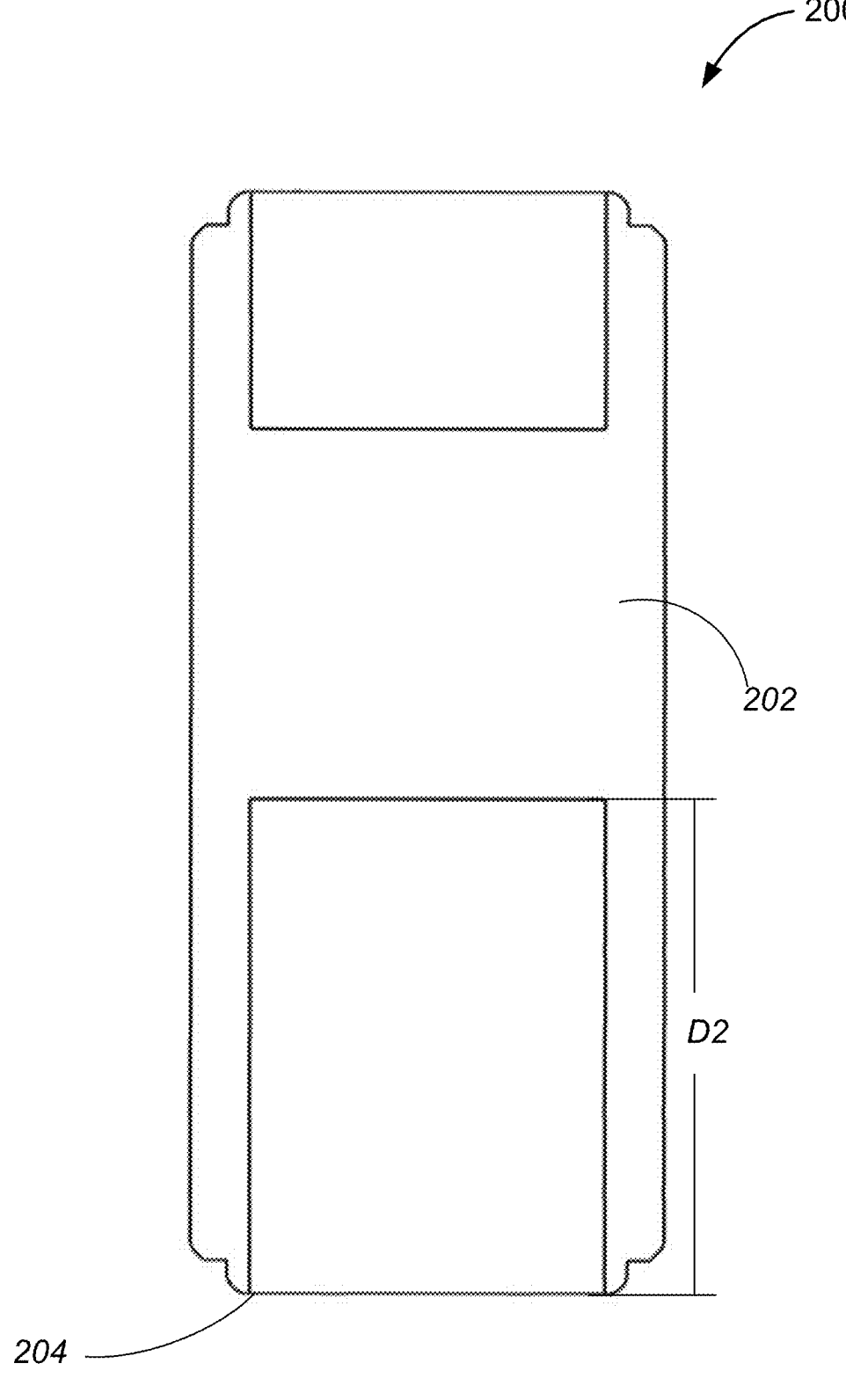
Figure 19:
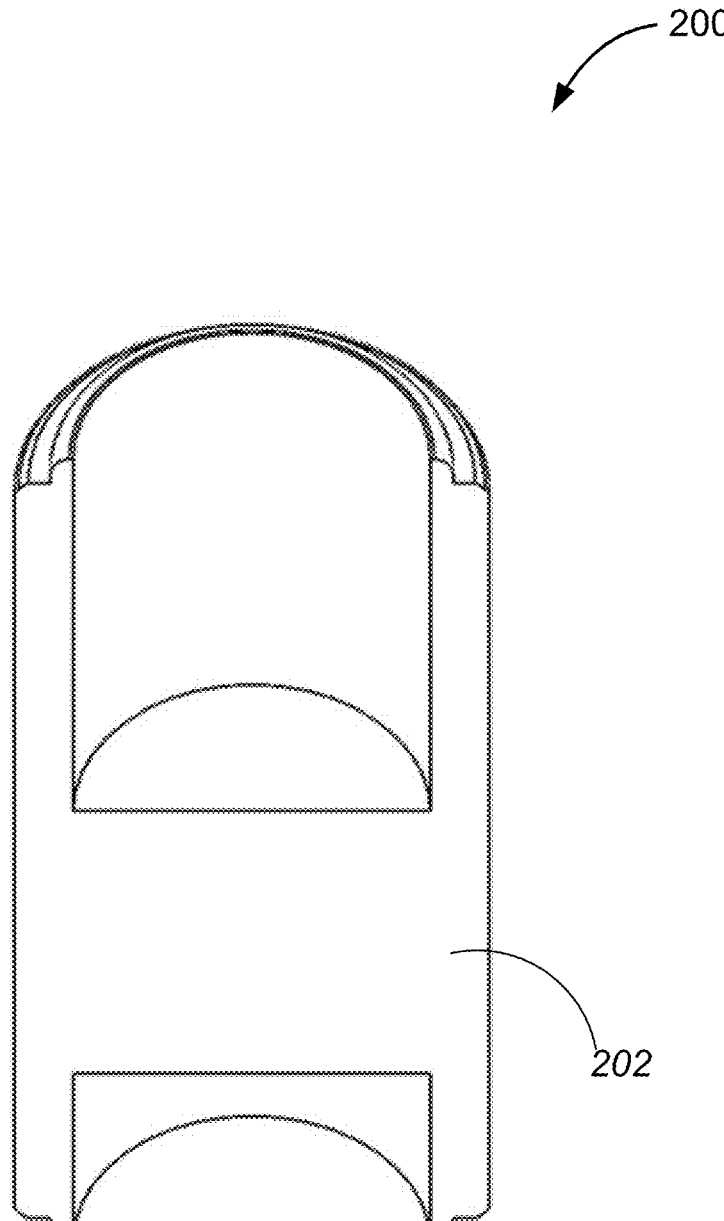
FIG. 19 is a side top perspective cross sectional view of the counterweight for a fractionation device as disclosed herein, with the cross section taken along a front to back centerline plane.

In various embodiments, the fractionation device 10 of FIGS. 1-16 may be included in a kit with a counterweight 200 shown in FIGS. 17-19. Alternatively, the counterweight 200 might be provided separately from the fractionation device 10. The counterweight 200 is configured to counterbalance or counterweight the fractionation device 10 in a centrifuge. In other words, the counterweight 200 is configured to counterbalance the fractionation device 10 when the fractionation device 10 is filled with blood or BMA, placed in a centrifuge, and is processed through one or more spin cycles within the centrifuge. The counterweight 200 might be formed from a solid piece of material (e.g., plastic, metal, rubber, or the like).

Because the fractionation device 10 is configured to be centrifuged in a first state (e.g., shown in FIGS. 14 and 15) with the blood or BMA in the lower chamber 56 and to be centrifuged in a second state (e.g., shown in FIG. 16) with portions of the blood or BMA in the upper chamber 54 (and optionally portions of the blood or BMA in the lower chamber 56), the fractionation device 10 has a first center of gravity in the first state and a second center of gravity in the second state. The counterweight 200 is configured to counterbalance both the first center of gravity in the first state and the second center of gravity in the second state of the fractionation device 10. In a first orientation, shown in FIG. 18A, the counterweight 200 is configured to counterbalance the fractionation device 10 in the first state (e.g., with the blood or BMA in the lower chamber 56). In a second orientation, shown in FIG. 18B, the counterweight is configured to counterbalance the fractionation device 10 in the second state (e.g., with portions of the blood or BMA in the upper chamber 54).

In order to counterbalance the first center of gravity of the fractionation device 10 in the first state, a middle portion 202 of the counterweight 200 is a first distance D1 away from a bottom 204 of the counterweight 200 in the first orientation. In order to counterbalance the second center of gravity of the fractionation device 10 in the second state, a middle portion 202 of the counterweight 200 is a second distance D2 away from a bottom 204 of the counterweight 200 in the second orientation. In this way, the counterweight 200 can be used to balance the centrifuge when the fractionation device 10 is in the first state or the second state.

Figure 20B:
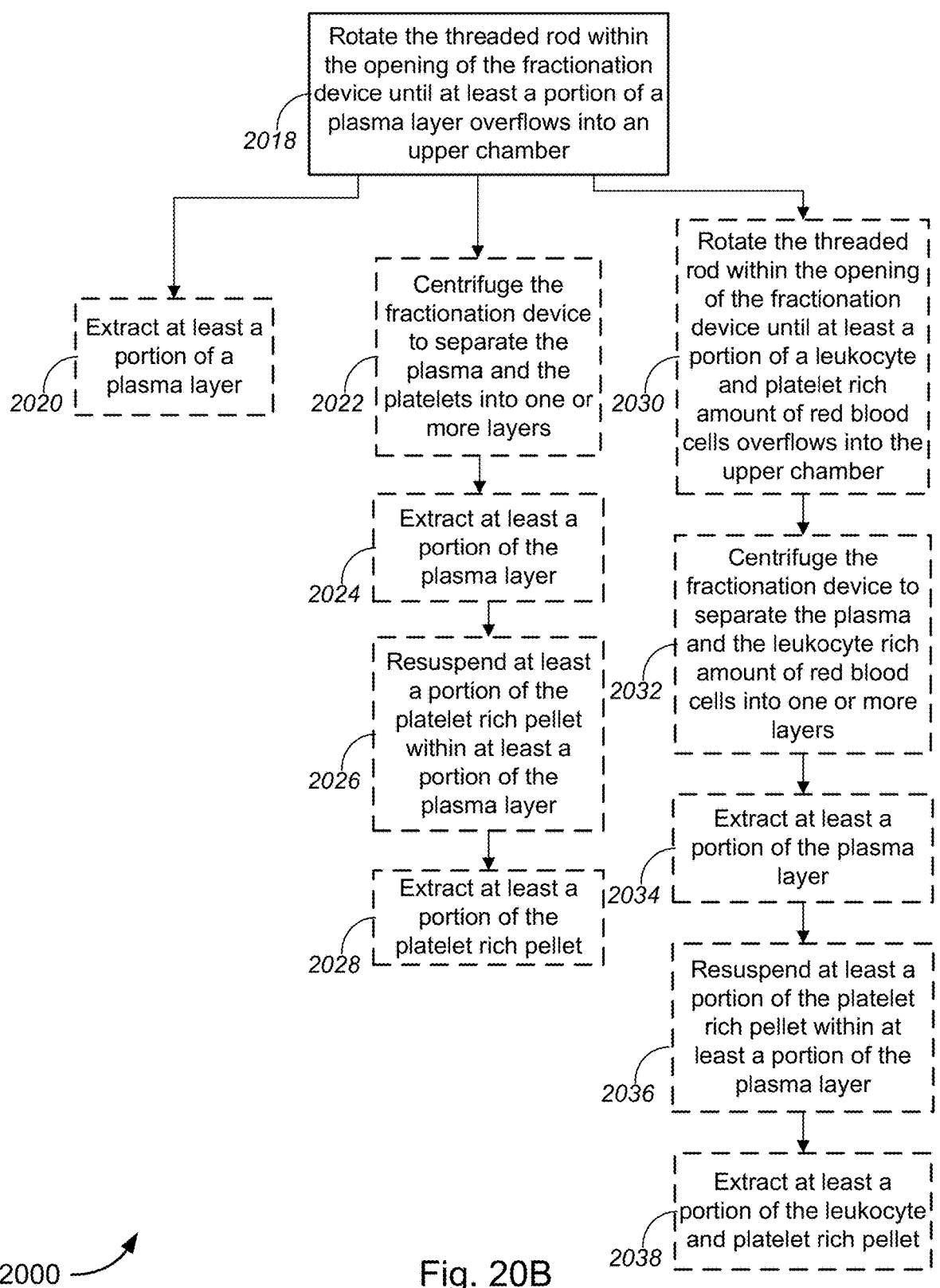

One alternative embodiment shown in FIGS. 20A and 20B is a method 2000 implemented to use the fractionation device 10 of FIGS. 1-16 and/or the counterweight 200 of FIGS. 17-19. Reference will also be made to FIGS. 14-16 to show the different layers or fractions of the blood, BMA, or other bodily fluids contained within the fractionation device 10 after some of the method steps. Additionally, although method 2000 will be described below with respect to blood or BMA, other bodily fluids might be processed in a similar manner using the fractionation device 10.

The method, at block (e.g., manual operation) 2002, includes providing a fractionation device 10 of FIGS. 1-16. Method 2000, at block 2004, includes obtaining blood or BMA from a patient. In certain embodiments, the blood or BMA is drawn from the patient and then processed in the fractionation device 10. Alternatively, the blood or BMA is drawn from the patient at an earlier date and stored before being processed in the fractionation device 10.

The blood or BMA may then be pretreated (optional block 2006). The pretreatment of the blood or BMA might include diluting the blood or BMA or adding an anticoagulant to the blood or BMA. Once pretreated, the blood or BMA, at block 2008, is inserted into a lower chamber 56 of the fractionation device 10. The blood or BMA is inserted into the lower chamber 56 via the first port 74 and the input channel 66. A technician or user of the fractionation device 10 might insert the blood or the BMA by directing the blood or BMA toward the inner sidewall surface 14 and flowing at least a portion of the blood or BMA down the sidewall indentation 70 into the lower chamber 56. Causing the blood or BMA to run along the sidewall indentation 70 reduces hemolysis of the blood or BMA or the formation of bubbles within the blood or the BMA and makes it easier to process the blood or the BMA.

Once the blood or the BMA is collected in the lower chamber 56, method 2000 includes, at block 2010, centrifuging the fractionation device 10 to separate the blood or the BMA into different layers or fractions. For blood, the layers comprise an erythrocyte layer or red blood cell layer 90, a buffy coat layer or leukocyte layer 92, and a plasma layer 94 shown in FIG. 11. For BMA, the layers comprise an erythrocyte layer or red blood cell layer 90, a buffy coat layer or leukocyte layer 92, a plasma layer 94, and a lipid layer 96 shown in FIG. 12. Sometimes platelets are located in the plasma layer 94, in other instances, platelets are located in the buffy coat or leukocyte layer 92, and, in other cases, platelets are located in both the plasma layer 94 and the buffy coat or leukocyte layer 92. During this first centrifuge cycle, the counterweight 200 in a first orientation (shown in FIG. 18A) might be used to counterbalance the fractionation device 10 in the centrifuge.

The method 2000, at block 2012, includes engaging a threaded rod 30 with opening 28 in bottom wall 24 and rotating, at block 2014, the threaded rod 30 within the opening 28 to cause the captive plunger 36 to rise within the lower chamber 56 of the fractionation device 10.

For BMA, the captive plunger 36 rises until the lipid layer 96 is in contact with the lipid layer collection tube 76 of the fractionation device 10b. Then, the method, at optional block 2016, includes extracting using the lipid layer collection tube 76 at least a portion or all of the lipid layer 96 from the fractionation device 10b.

For blood or for BMA (after at least a portion or all of the lipid layer 90 has been extracted from the fractionation device 10b), the method, at block 2018, includes rotating the threaded rod 30 within the opening 28 to cause the captive plunger 36 to rise within the lower chamber 56 of the fractionation device 10 until at least a portion or all of the plasma layer 94 overflows into the upper chamber 54 of the fractionation device 10 via the overflow window 72 formed in the vertical portion 46 of the interior partition 44 and providing a fluid pathway between the input channel 66 and the upper chamber 54. Graduated lines 102 may be formed on the fractionation device 10 for a user to use to measure an amount of the plasma layer 94 to overflow into the upper chamber 54.

In various instances, a technician or user of the fractionation device 10 might only want to extract at least a portion or all of the plasma layer 94. In this case, the technician may the extract at least a portion or all of the plasma layer 94 from the fractionation device 10 via the plasma layer collection tube 80 and the second port 78 at optional block 2020.

In other cases, a technician or user of the fractionation device 10 might want to extract platelets from the plasma layer 94. In this case, a first graduated line 102a may be used to determine an amount of the plasma layer 94 (containing platelets) to overflow into the upper chamber 54. In a non-limiting example, the threaded rod 30 might be rotated until a lower portion of the plasma layer 94 reaches the first graduated line 102a. This allows the majority of the plasma layer 94 (containing platelets) to overflow into the upper chamber 54 while minimizing an amount of leukocytes from the leukocyte layer 92 from entering the upper chamber 54.

In some instances, the threads on the threaded rod 30 and/or the orientation of the prongs 34 on the knob 32 may be used to cause a predetermined amount of the plasma layer 94 (containing platelets) to overflow into the upper chamber 54.

Next, at optional block 2022, the method might include centrifuging the plasma layer to separate the plasma layer 94 into an upper chamber plasma layer 98 and a platelet rich pellet layer 100 shown in FIG. 16. The sloped portion 48 and the one or more sloped indentations 62 in the sidewall 12 of the fractionation device 10 work with the centrifuge to collect the platelet rich pellet layer 100 in the lower region 58. During this second centrifuge cycle, the counterweight 200 in a second orientation (shown in FIG. 18B) might be used to counterbalance the fractionation device 10 in the centrifuge.

The method 2000, at optional block 2024, then includes removing at least a portion or all of the upper chamber plasma layer 98 via the plasma layer collection tube 80 and the second port 78. Next, the method 2000 includes optionally resuspending or mixing the platelet rich pellet 100 within a portion of upper chamber plasma layer 98 (optional block 2026) and removing at least a portion of the platelet rich pellet layer 100 (optionally mixed with at least a portion of the upper chamber plasma layer 98) from the upper chamber 54 via the platelet rich pellet layer and/or leukocyte and platelet rich pellet layer collection tube 84 and the third port 82 (optional block 2028). In a non-limiting example, the platelet rich pellet layer 100 might be mixed with at least a portion of the upper chamber plasma layer 98 using the platelet rich pellet layer and/or leukocyte and platelet rich pellet layer collection tube 84 before being removed. In some instances, one or more graduated lines 102 may be formed on the upper chamber 54 sidewall 12 to aid a user to determine an amount of the upper chamber plasma layer 98 to mix with the platelet rich pellet layer 100. Alternatively, only at least a portion or all of the platelet rich pellet layer 100 might be removed without or with a minimal amount of the upper chamber plasma layer 98.

In other cases, a technician or user of the fractionation device 10 might want to include at least a portion or all of the buffy coat layer or platelet and leukocyte layer 92 with the plasma layer 94 in the upper chamber 54. In this case, the method 2000 includes, at optional block 2030, further rotating the threaded rod 30 so that a leukocyte and platelet rich amount of red blood cells (e.g., at least a portion or all of the buffy coat layer or platelet and leukocyte layer 92) enter the upper chamber 54 of the fractionation device 10 via the overflow window 72. A second graduated line 102b may be used to determine an amount of the plasma layer 94 (containing platelets or platelet poor) and the buffy coat or leukocyte layer 92 (containing platelets or platelet poor) to overflow into the upper chamber 54. In a non-limiting example, the threaded rod 30 might be rotated until a lower portion of the plasma layer 94 reaches the second graduated line 102b. Then the threaded rod 30 may be oriented such that a prong 34 faces a user. Next, the threaded rod 30 may be rotated (e.g., a quarter turn, half turn, etc.) such that an amount of the buffy coat or leukocyte layer 92 enters the upper chamber 54. This allows the plasma layer 94 and at least a portion of the buffy coat or leukocyte layer 92 to overflow into the upper chamber 54 while minimizing the amount of red blood cells from the erythrocyte layer or red blood cell layer 90 from entering the upper chamber 54. In some instances, the threads on the threaded rod 30 and/or the orientation of the prongs 34 of the knob 32 may be used to cause a predetermined amount of the plasma layer 94 and/or an amount of the buffy coat or leukocyte layer 92 to overflow into the upper chamber 54.

After rotating the threaded rod 30 so that a leukocyte and platelet rich amount of red blood cells enter the upper chamber 54, the method continues, at optional block 2032, by removing the threaded rod 30 from the fractionation device 10 and centrifuging the fractionation device 10 to separate the plasma layer 94 located in the upper chamber 54 and the leukocyte rich amount of red blood cells into one or more layers including a upper chamber plasma layer 98 and a leukocyte and platelet rich pellet layer 100 shown in FIG. 16. The sloped portion 48 and the one or more sloped indentations 62 in the sidewall 12 of the fractionation device 10 work with the centrifuge to collect the leukocyte and platelet rich pellet layer 100 in the lower region 58. During this second centrifuge cycle, the counterweight 200 in a second orientation (shown in FIG. 18B) might be used to counterbalance the fractionation device 10 in the centrifuge.

The method 2000, at optional block 2034, then includes removing at least a portion or all of the upper chamber plasma layer 98 via the plasma layer collection tube 80 and the second port 78. Next, the method 2000 includes optionally resuspending or mixing the leukocyte and platelet rich pellet 100 within a portion of upper chamber plasma layer 98 (optional block 2036) and removing at least a portion of the leukocyte and platelet rich pellet layer 100 (optionally mixed with at least a portion of the upper chamber plasma layer 98) from the upper chamber 54 via the platelet rich pellet layer and/or leukocyte and platelet rich pellet layer collection tube 84 and the third port 82 (optional block 2038). In some instances, the leukocyte and platelet rich pellet layer 100 might be mixed with at least a portion of the upper chamber plasma layer 98 using the platelet rich pellet layer and/or leukocyte and platelet rich pellet layer collection tube 84 before being removed. In some instances, one or more graduated lines may be formed on the upper chamber 54 sidewall 12 to aid a user to determine an amount of the upper chamber plasma layer 98 to mix with the leukocyte and platelet rich pellet layer 100. Alternatively, only at least a portion or all of the leukocyte and platelet rich pellet layer 100 might be removed without or with a minimal amount of the upper chamber plasma layer 98.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

The previous description of the disclosed embodiments is provided to enable any person skilled in the art to make or use the invention. Various modifications to these embodiments will be readily apparent to those skilled in the art, and the generic principles defined herein may be applied to other embodiments without departing from the spirit or scope of the invention. Thus, the invention is not intended to be limited to the embodiments shown herein but is to be accorded the widest scope consistent with the principles and novel features disclosed herein.

What is claimed is:

1. A fractionation device comprising:
a sidewall, the sidewall having a generally cylindrical profile;
a top wall connected to an upper portion of the sidewall;
a bottom wall connected to a lower portion of the sidewall;
an interior partition comprising:
a sloped portion contacting the sidewall; and a vertical portion contacting the top wall;
an upper chamber defined within the fractionation device by the interior partition, the top wall, and the upper portion of the sidewall;
a lower chamber defined within the fractionation device by the interior partition, an upper plunger surface of a captive plunger engaged with the sidewall, and the lower portion of the sidewall;
a lower region of the upper chamber defined by the sloped portion of the interior partition adjacent to the sidewall;
a sloped indentation formed in the sidewall, the sloped indentation defining a side of the sloped portion and causing the sloped portion to become narrower toward the lower region; and
a threaded opening formed in and through the bottom wall.

2. The fractionation device of claim 1 further comprising:
an input channel extending from the top wall to the lower chamber; and
an overflow window at least partially formed in the vertical portion of the interior partition and providing a fluid pathway between the input channel and the upper chamber, wherein the top wall defines an upper boundary of the overflow window.

3. The fractionation device of claim 2, wherein the input channel is defined in part by the vertical portion of the interior partition and the upper portion of the sidewall.

4. The fractionation device of claim 3 further comprising:
one or more input channel indentations in the sidewall at the input channel to restrict a horizontal cross section of the input channel, wherein the one or more input channel indentations curve inward into the input channel toward the vertical portion.

5. The fractionation device of claim 3 further comprising:
a plurality of ports extending through the top wall.

6. The fractionation device of claim 5 further comprising:
a first port of the plurality of ports opening into the input channel; and
an indentation in the sidewall causing a portion of the sidewall to extend toward the vertical portion of the interior partition within the input channel and under the first port.

7. The fractionation device of claim 6 further comprising:
a lipid layer collection tube extending from the first port toward the lower chamber and having a length configured to extract at least a portion of the lipid layer.

8. The fractionation device of claim 7 further comprising:
a second port of the plurality of ports opening into the upper chamber adjacent to the vertical portion of the interior partition; and
a plasma layer collection tube extending from the second port to a position within the upper chamber and having a length configured to extract at least a portion of the plasma layer.

9. The fractionation device of claim 8 further comprising:
a third port of the plurality of ports opening into the upper chamber adjacent to the sidewall and above the lower region of the upper chamber; and
a leukocyte and platelet layer collection tube extending from the third port to a position above the lower region of the upper chamber and having a length configured to extract at least a portion of the leukocyte and platelet layer.

10. The fractionation device of claim 1, wherein the lower region of the upper chamber defined by the sloped portion of the interior partition adjacent to the sidewall comprises a flat portion configured to collect a platelet rich pellet layer or a leukocyte and platelet rich pellet layer, wherein the flat portion is a narrowest region of the sloped portion.

11. The fractionation device of claim 1, wherein the sidewall is fabricated from an optically transparent material.

12. The fractionation device of claim 1 further comprising:

a threaded rod having threads sized to engage with the threaded opening.

13. A method of collecting a blood or bone marrow aspirate (BMA) fraction, the method comprising:

providing a fractionation device comprising:

a sidewall, the sidewall having a generally cylindrical profile;

a top wall connected to an upper portion of the sidewall;

a bottom wall connected to a lower portion of the sidewall;

an interior partition comprising:

a sloped portion contacting the sidewall; and a vertical portion contacting the top wall;

an upper chamber defined within the fractionation device by the interior partition, the top wall, and the upper portion of the sidewall;

a lower chamber defined within the fractionation device by the interior partition, an upper plunger surface of a captive plunger engaged with the sidewall, and the lower portion of the sidewall;

a lower region of the upper chamber defined by the sloped portion of the interior partition adjacent to the sidewall;

a sloped indentation formed in the sidewall, the sloped indentation defining a side of the sloped portion and causing the sloped portion to become narrower toward the lower region; and a threaded opening formed in and through the bottom wall;

obtaining blood or bone marrow aspirate (BMA) from a patient;

pretreating the blood or the BMA from the patient;

inserting the blood or the BMA into the lower chamber of the fractionation device;

centrifuging the fractionation device in a first centrifuge cycle to separate the blood or the BMA into different layers;

engaging a threaded rod with the threaded opening;

rotating the threaded rod within the threaded opening to cause the captive plunger to rise within the lower chamber of the fractionation device until a plasma layer overflows into the upper chamber of the fractionation device via an overflow window formed in the vertical portion of the interior partition and providing a fluid pathway between an input channel and the upper chamber; and removing at least a portion of the plasma layer from the upper chamber of the fractionation device.

14. The method of claim 13, wherein the blood or the BMA is inserted into the fractionation device via the input channel extending from the top wall to the lower chamber.

15. The method of claim 13, wherein, when BMA is used, the threaded rod is first rotated to cause a lipid layer to rise to a lipid layer collection tube extending from a first port toward the lower chamber, wherein the first port opens into the input channel, the method further comprising:

removing at least a portion of the lipid layer via the lipid layer collection tube from the fractionation device.

16. The method of claim 13, further comprising:

after rotating the threaded rod within the threaded opening to cause the captive plunger to rise within the lower chamber of the fractionation device until the plasma layer overflows into the upper chamber of the fractionation device via the overflow window, further rotating the threaded rod so that a leukocyte and platelet rich amount of red blood cells enter the upper chamber;

after rotating the threaded rod so that a leukocyte and platelet rich amount of red blood cells enter the upper chamber, removing the threaded rod from the fractionation device and centrifuging the fractionation device in a second centrifuge cycle to separate the plasma layer and the leukocyte and platelet rich amount of red blood cells into one or more layers including a leukocyte and platelet rich pellet;

removing at least the portion of the plasma layer from the upper chamber; and removing at least a portion of the leukocyte and platelet rich pellet from the upper chamber.

17. The method of claim 16, wherein at least the portion of the plasma layer is removed from the upper chamber of the fractionation device via a second port opening into the upper chamber adjacent to the vertical portion of the interior partition and via a plasma layer collection tube extending from the second port to a position within the upper chamber.

18. The method of claim 17, wherein at least the portion of the leukocyte and platelet rich pellet is removed via a third port opening into the upper chamber adjacent to the sidewall and above the lower region of the upper chamber via a leukocyte and platelet layer collection tube extending from the third port to a position above the lower region of the upper chamber.

19. The method of claim 18, wherein at least the portion of the leukocyte and platelet rich pellet is collected in the lower region of the upper chamber.

20. The method of claim 19, wherein the lower region of the upper chamber defined by the sloped portion of the interior partition adjacent to the sidewall comprises a flat portion configured to collect the leukocyte and platelet rich pellet, and wherein at least the portion of the leukocyte and platelet rich pellet that is collected in the lower region of the upper chamber is disposed over the flat portion of the sloped portion of the interior partition.

21. The method of claim 16, further comprising:

providing a counterweight configured to counterbalance the fractionation device and having a first center of gravity in a first orientation and a second center of gravity in a second orientation;

wherein, during the first centrifuge cycle, the counterweight is in the first orientation and, during the second centrifuge cycle, the counterweight is in the second orientation.

22. A system comprising:

a fractionation device comprising:

a sidewall, the sidewall having a generally cylindrical profile;

a top wall connected to an upper portion of the sidewall;

a bottom wall connected to a lower portion of the sidewall;

an interior partition comprising:

a sloped portion contacting the sidewall; and a vertical portion contacting the top wall;

an upper chamber defined within the fractionation device by the interior partition, the top wall, and the upper portion of the sidewall;

a lower chamber defined within the fractionation device
by the interior partition, an upper plunger surface of
a captive plunger engaged with the sidewall, and the
lower portion of the sidewall;

a lower region of the upper chamber defined by the
sloped portion of the interior partition adjacent to the
sidewall;

a sloped indentation formed in the sidewall, the sloped
indentation defining a side of the sloped portion and
causing the sloped portion to become narrower
toward the lower region; and a threaded opening formed in and through the bottom
wall;

a centrifuge configured to receive the fractionation
device; and a counterweight configured to be placed in the centrifuge
opposite the fractionation device to counterbalance the
fractionation device and having a first center of gravity
in a first orientation and a second center of gravity in a
second orientation.

* * * * *